United States Patent
Amano et al.

(10) Patent No.: US 6,334,850 B1
(45) Date of Patent: Jan. 1, 2002

(54) METHOD OF DETECTING PULSE WAVE, METHOD OF DETECTING ARTERY POSITION, AND PULSE WAVE DETECTING APPARATUS

(75) Inventors: Kazuhiko Amano; Kazuo Uebaba, both of Yokohama; Hitoshi Ishiyama, Toride, all of (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 09/341,248

(22) PCT Filed: Nov. 19, 1998

(86) PCT No.: PCT/JP98/05189
§ 371 Date: Aug. 19, 1999
§ 102(e) Date: Aug. 19, 1999

(87) PCT Pub. No.: WO99/25242
PCT Pub. Date: May 27, 1999

(30) Foreign Application Priority Data

Nov. 19, 1997 (JP) .............................. 9-318628

(51) Int. Cl.$^7$ ................................. A61B 5/02
(52) U.S. Cl. ......................................... 600/500
(58) Field of Search ........................ 600/500, 501, 600/502, 503

(56) References Cited

U.S. PATENT DOCUMENTS

| | | | | |
|---|---|---|---|---|
| 4,802,486 A | * | 2/1989 | Goodman et al. | 600/500 |
| 4,901,733 A | * | 2/1990 | Kaida et al. | 600/500 |
| 4,928,692 A | * | 5/1990 | Goodman et al. | 600/500 |
| 4,951,679 A | | 8/1990 | Harada | |
| 5,170,796 A | | 12/1992 | Kobayashi | |
| 5,876,346 A | * | 3/1999 | Corso | 600/500 |

FOREIGN PATENT DOCUMENTS

| | | |
|---|---|---|
| EP | 0 947 160 A1 | 10/1999 |
| JP | 2-1226 | 5/1990 |
| JP | 7-299043 | 11/1995 |

OTHER PUBLICATIONS

"Application of Wavelet Transformation To Wave Pulse Of Living Body (In Japanese)", Preprint of 15$^{th}$ Scientific Lectures on Biomechanism, (Japan), (1994), pp. 121–124.

* cited by examiner

Primary Examiner—Cary O'Connor
Assistant Examiner—Navin Natnithithadha

(57) ABSTRACT

An optical type pulse wave detection section 1 detects the pulse waveform MH above the skin while moving in the circumferential direction of the arm, when a manual position change mechanism 2 is operated. Capillary vessels and arterioles surrounding a radial artery 24 are formed inside the skin, and pulsation of the capillary vessels and arterioles are opposite in polarity. When a polarity detection section 3 outputs a polarity detection signal KS showing the polarity of the pulse waveform MH, the polarity is displayed on a display 4. Accordingly, a subject can position the pulse wave detection section 1 above the arterioles surrounding the artery by operating the manual position change mechanism 2 while observing the display 4, allowing the pulse waveform MH to be detected with an optimal SN ratio. In addition, the pulse waveform of the arterioles can be detected by specifying the position of the artery without causing a constrictive feeling to the subject.

23 Claims, 13 Drawing Sheets

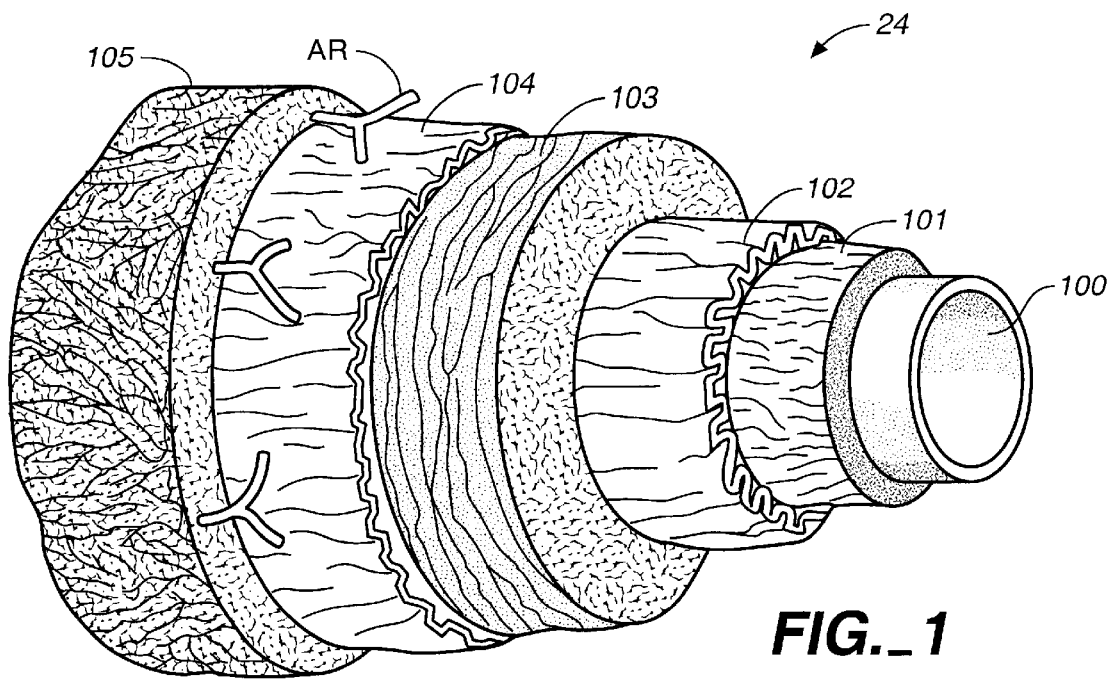
FIG._1
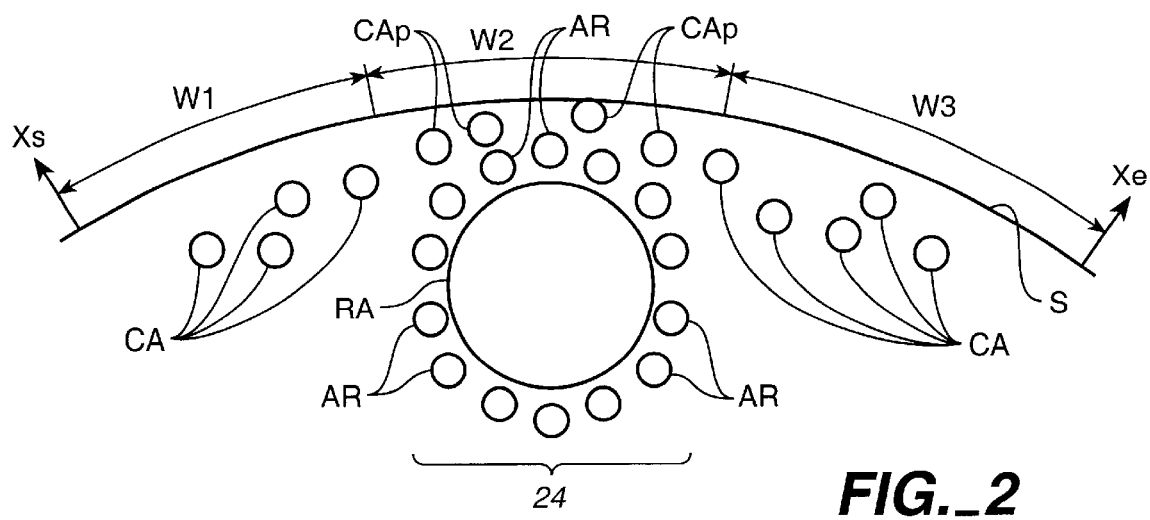
FIG._2

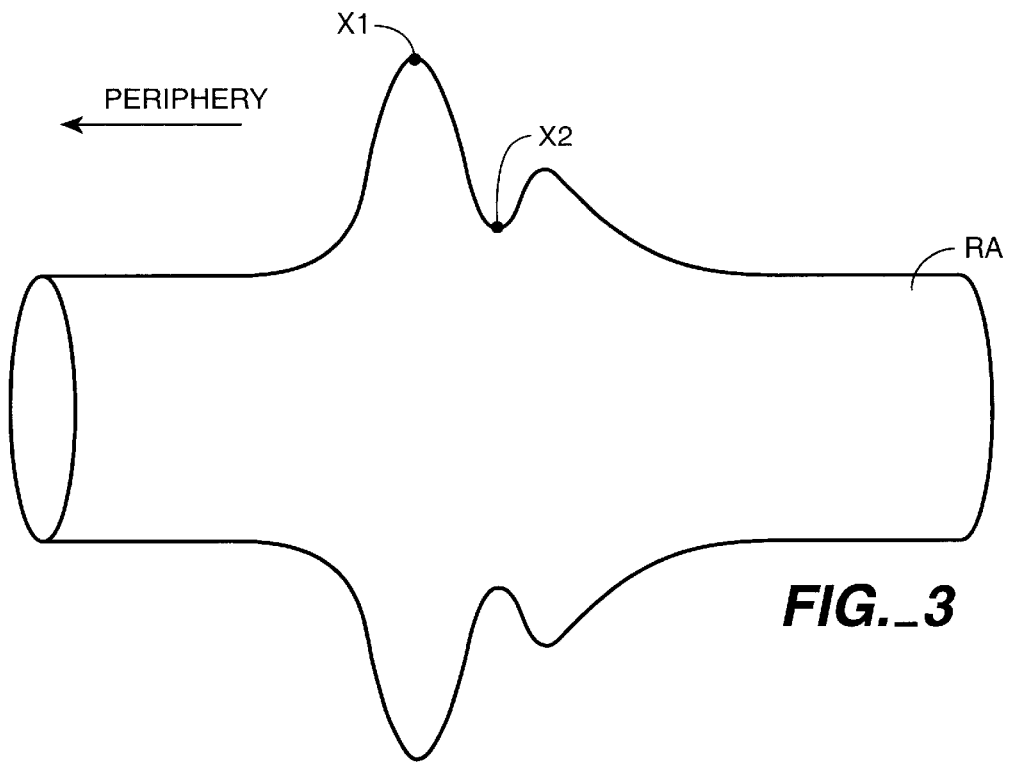
FIG._3
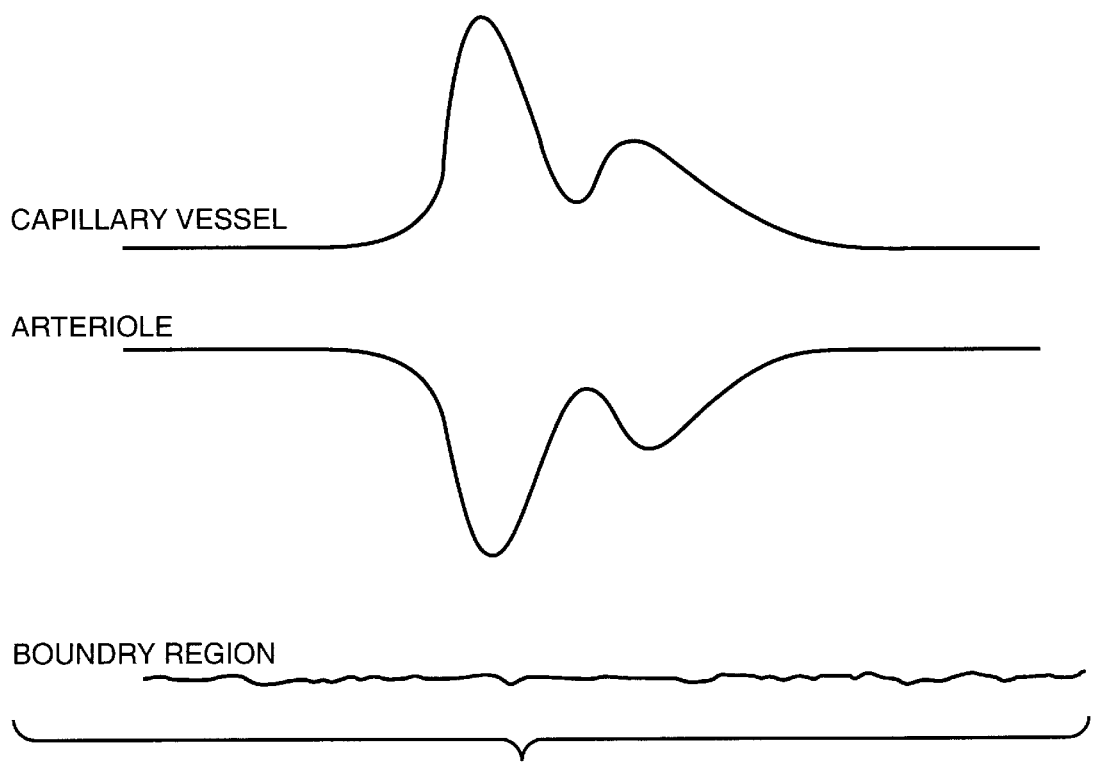
CAPILLARY VESSEL
ARTERIOLE
BOUNDRY REGION
FIG._4

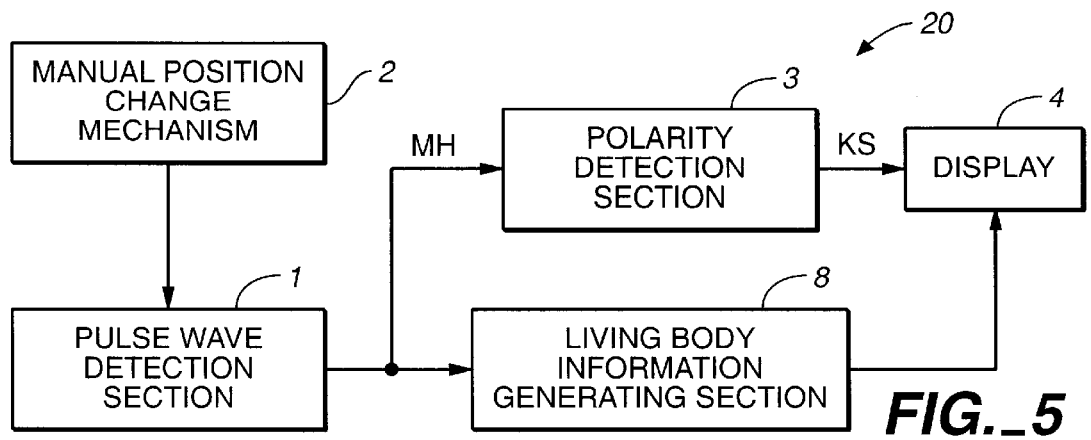
FIG._5
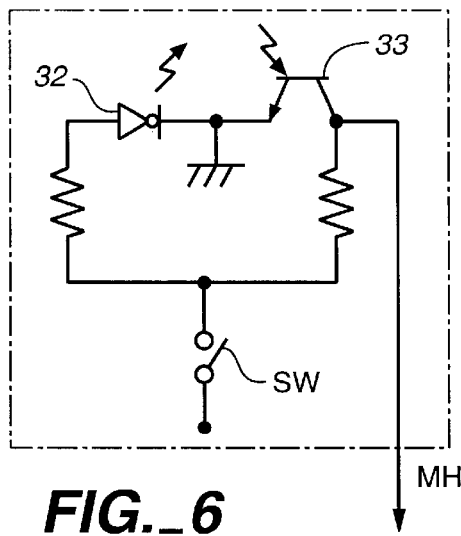
FIG._6
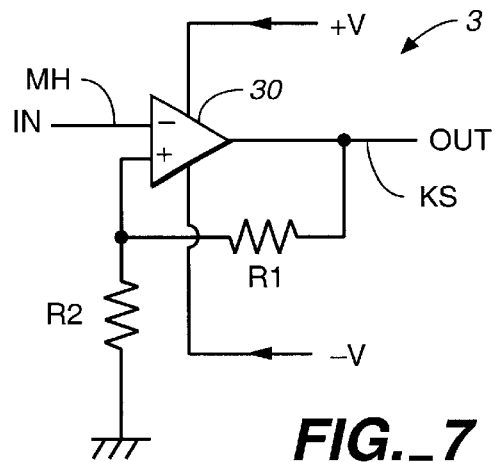
FIG._7
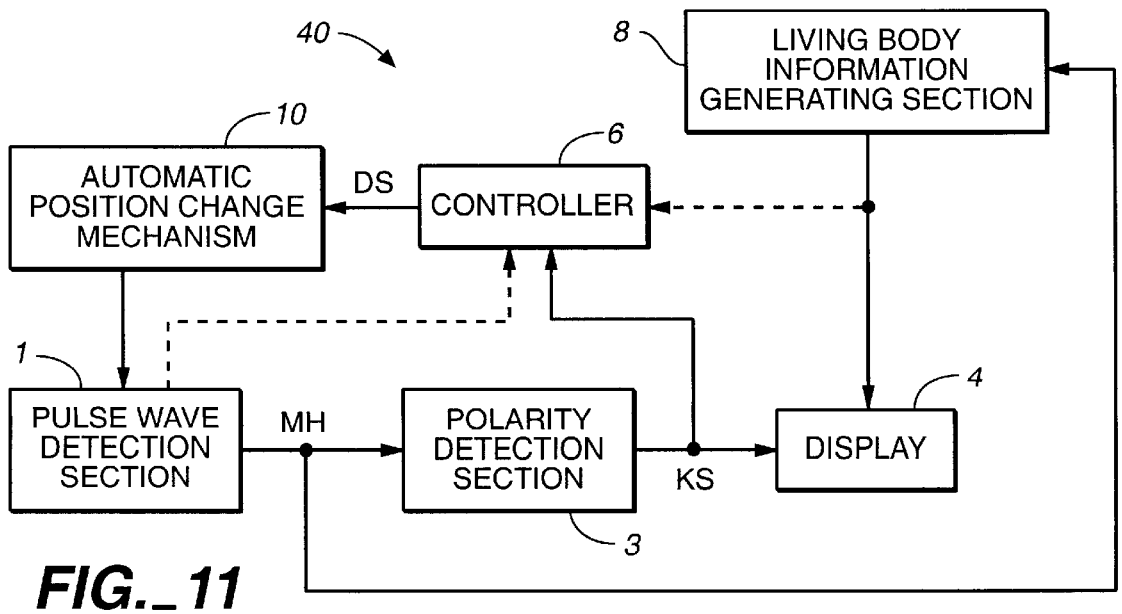
FIG._11

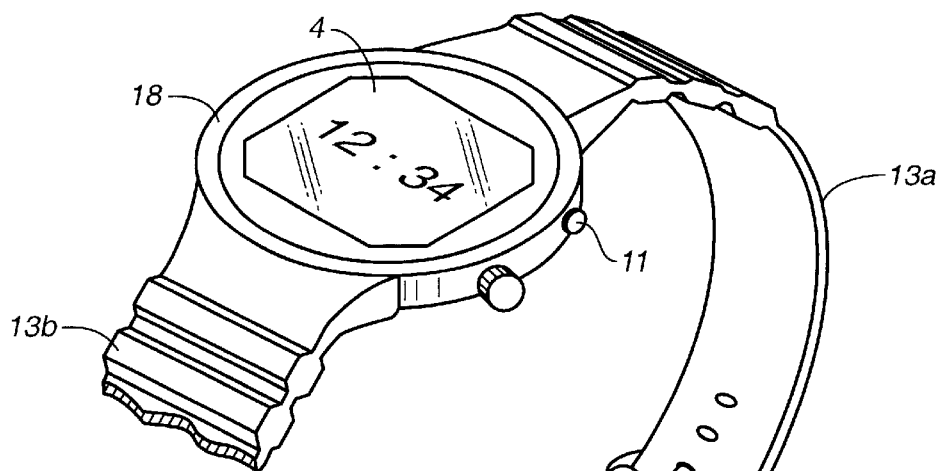
FIG._8
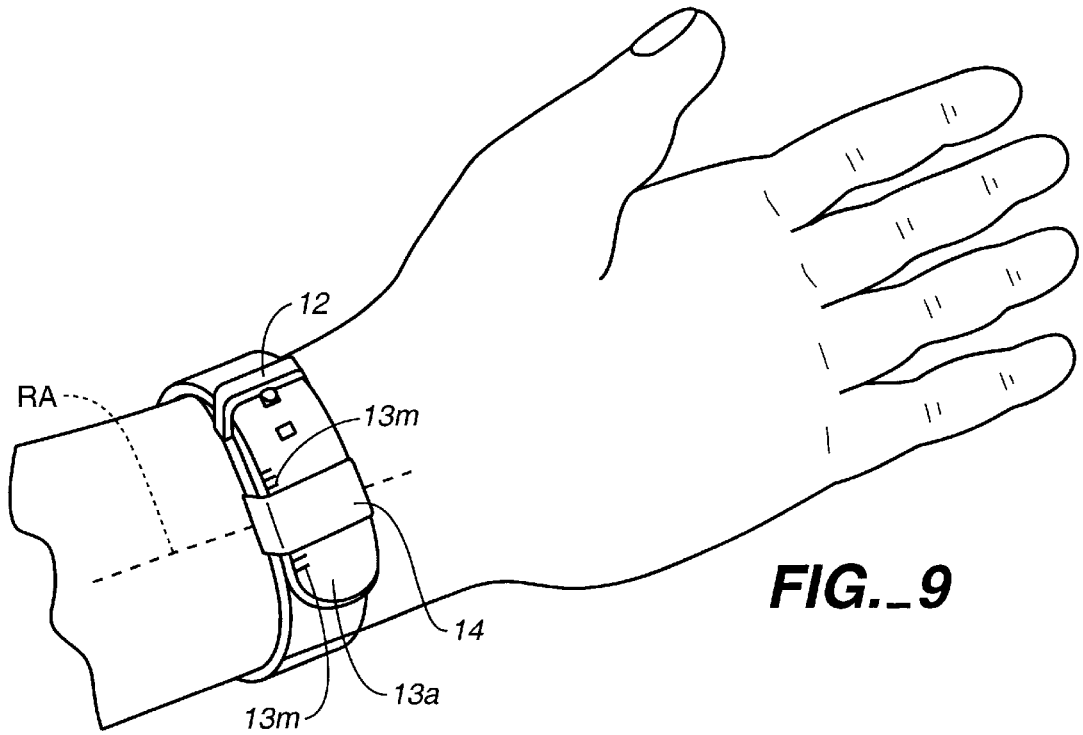
FIG._9

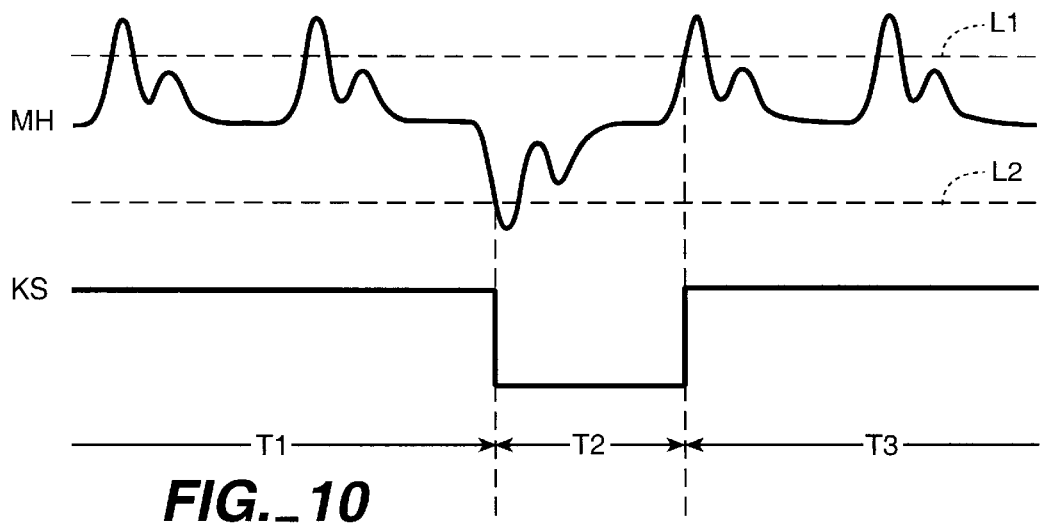
FIG._10
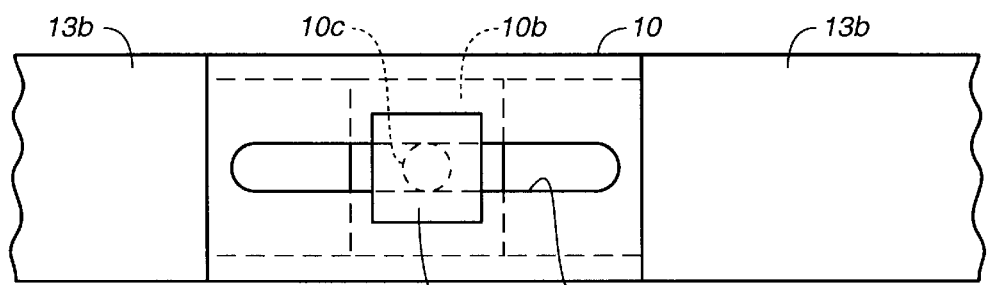
FIG._12
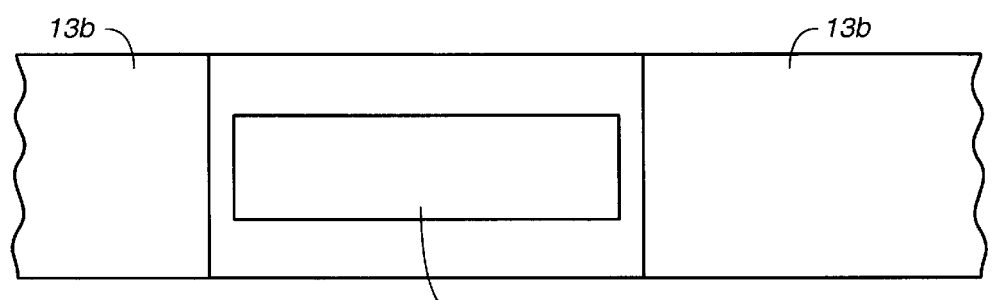
FIG._13
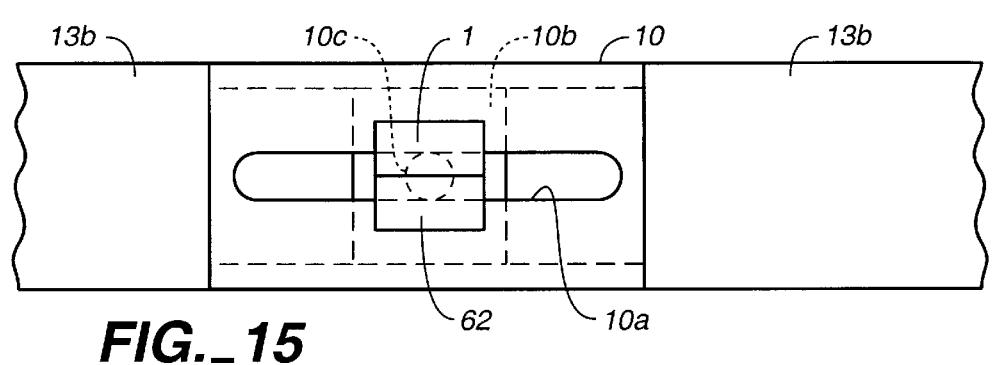
FIG._15

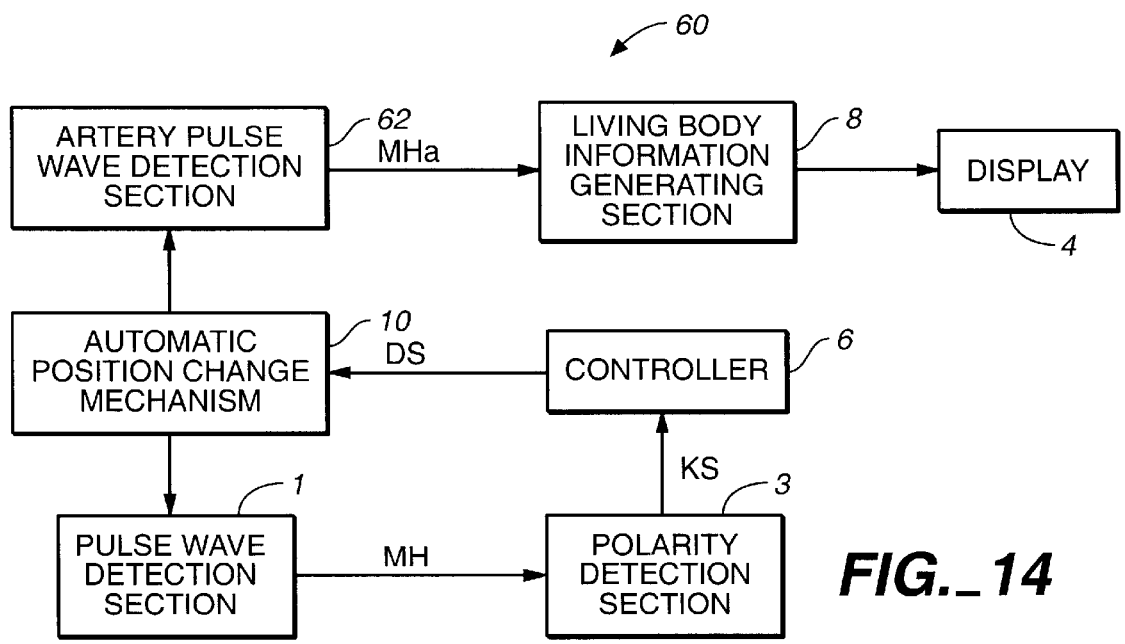
FIG._14
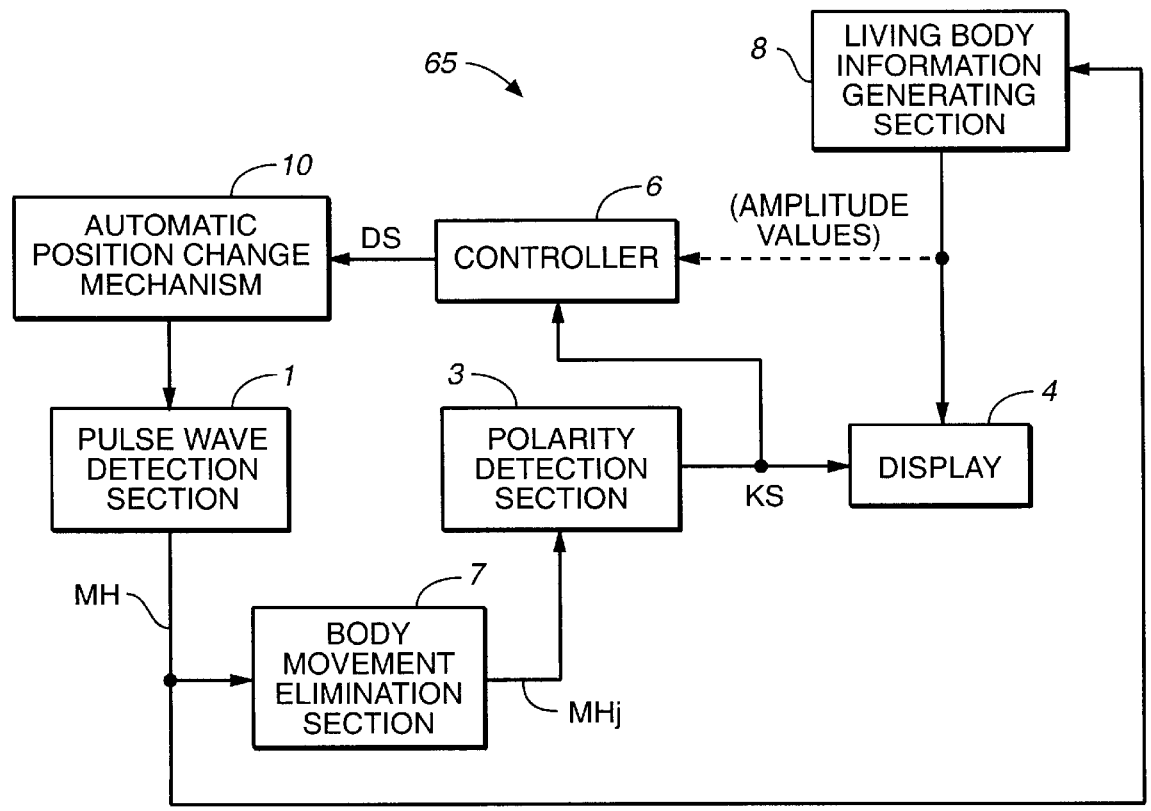
FIG._16

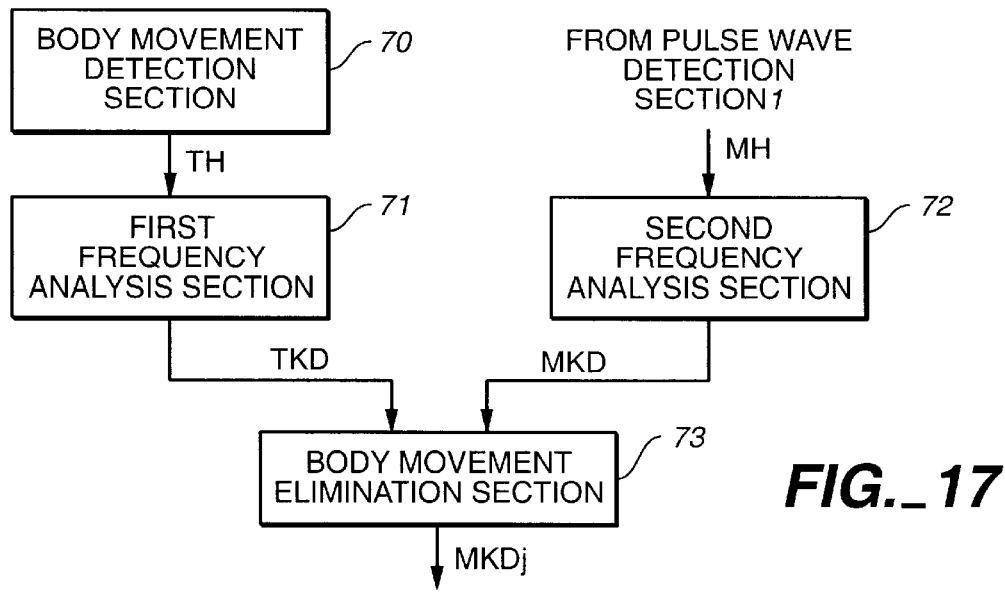
FIG._17
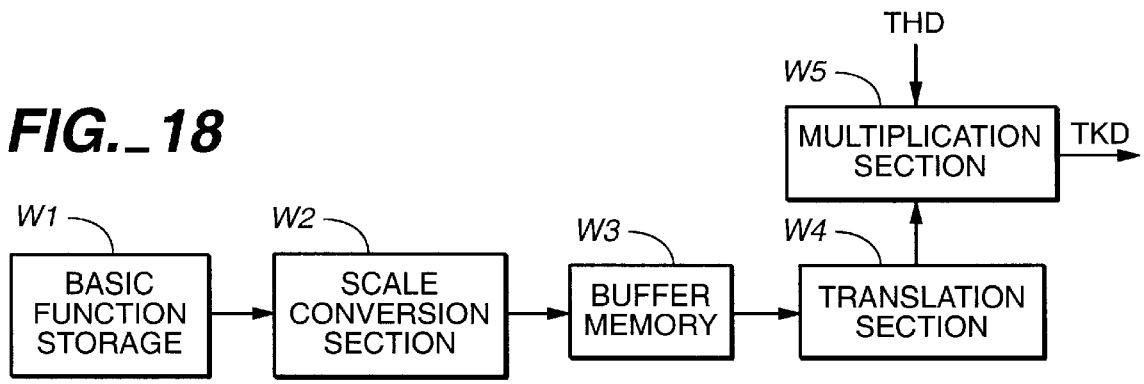
FIG._18
| | t1 | t2 | t3 | t4 | t5 | t6 | t7 | t8 |
|---|---|---|---|---|---|---|---|---|
| 4.0~3.5Hz | 8 | 4 | 6 | 0 | 0 | 0 | 0 | 0 |
| 3.5~3.0Hz | 5 | 2 | 3 | 1 | 0 | 0 | 0 | 0 |
| 3.0~2.5Hz | 2 | 1 | 4 | 0 | 0 | 0 | 0 | 0 |
| 2.5~2.0Hz | 1 | 1 | 3 | 0 | 1 | 0 | 0 | 1 |
| 2.0~1.5Hz | 2 | 3 | 1 | 1 | 1 | 0 | 0 | 1 |
| 1.5~1.0Hz | 4 | 5 | 5 | 5 | 5 | 6 | 5 | 4 |
| 1.0~0.5Hz | 4 | 7 | 8 | 8 | 6 | 8 | 8 | 8 |
| 0.5~0.0Hz | 6 | 7 | 7 | 10 | 10 | 9 | 9 | 9 |
FIG._20

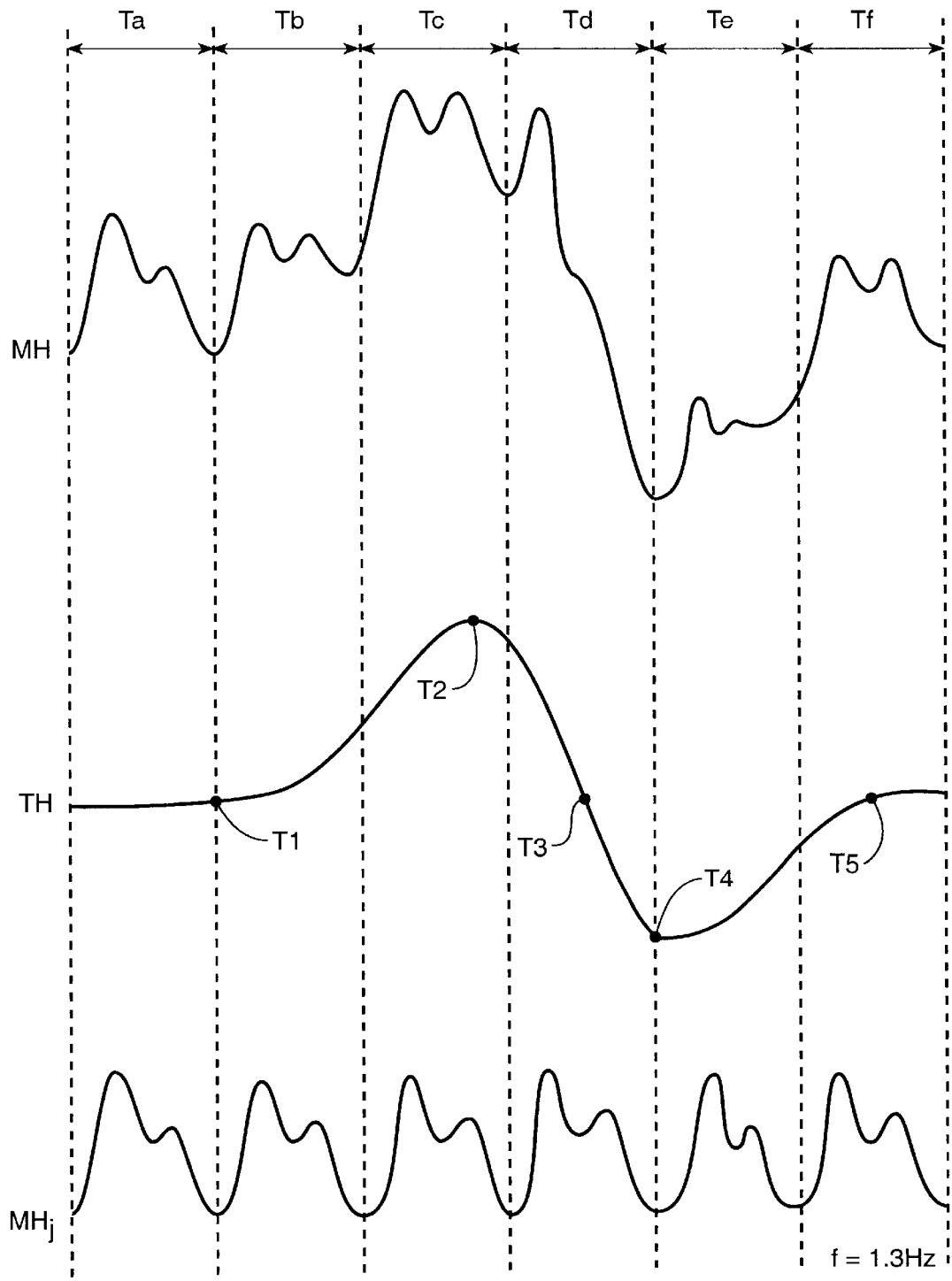
FIG._19

| | t1 | t2 | t3 | t4 | t5 | t6 | t7 | t8 |
|---|---|---|---|---|---|---|---|---|
| 4.0~3.5Hz | 0 | 0 | 0 | 0 | 0 | 0 | 0 | 0 |
| 3.5~3.0Hz | 0 | 0 | 0 | 0 | 0 | 0 | 0 | 0 |
| 3.0~2.5Hz | 0 | 0 | 0 | 0 | 0 | 0 | 0 | 0 |
| 2.5~2.0Hz | 0 | 0 | 0 | 0 | 0 | 0 | 0 | 0 |
| 2.0~1.5Hz | 0 | 0 | 0 | 0 | 0 | 1 | 0 | 0 |
| 1.5~1.0Hz | 0 | 1 | 1 | 0 | 0 | 2 | 1 | 0 |
| 1.0~0.5Hz | 4 | 5 | 7 | 7 | 5 | 6 | 6 | 7 |
| 0.5~0.0Hz | 5 | 6 | 6 | 6 | 7 | 6 | 6 | 6 |

FIG._21

| | t1 | t2 | t3 | t4 | t5 | t6 | t7 | t8 |
|---|---|---|---|---|---|---|---|---|
| 4.0~3.5Hz | 8 | 4 | 6 | 0 | 0 | 0 | 0 | 0 |
| 3.5~3.0Hz | 5 | 2 | 3 | 1 | 0 | 0 | 0 | 0 |
| 3.0~2.5Hz | 2 | 1 | 4 | 0 | 0 | 0 | 0 | 0 |
| 2.5~2.0Hz | 1 | 1 | 3 | 0 | 1 | 0 | 0 | 0 |
| 2.0~1.5Hz | 2 | 3 | 1 | 1 | 1 | 0 | 0 | 1 |
| 1.5~1.0Hz | 4 | 4 | 4 | 5 | 5 | 4 | 4 | 4 |
| 1.0~0.5Hz | 0 | 2 | 1 | 1 | 1 | 2 | 2 | 1 |
| 0.5~0.0Hz | 1 | 1 | 1 | 4 | 3 | 3 | 3 | 3 |

FIG._22

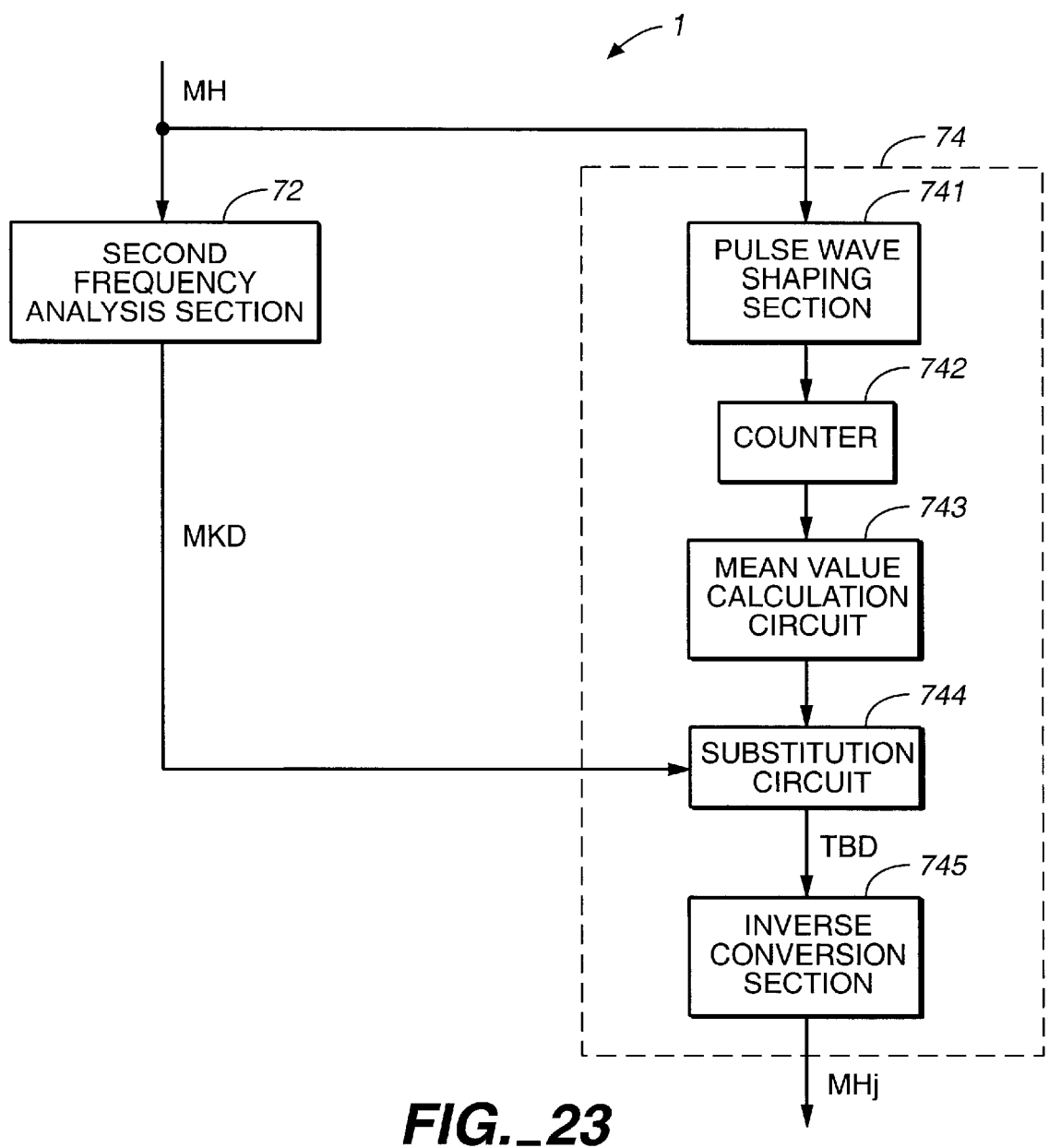
FIG._23

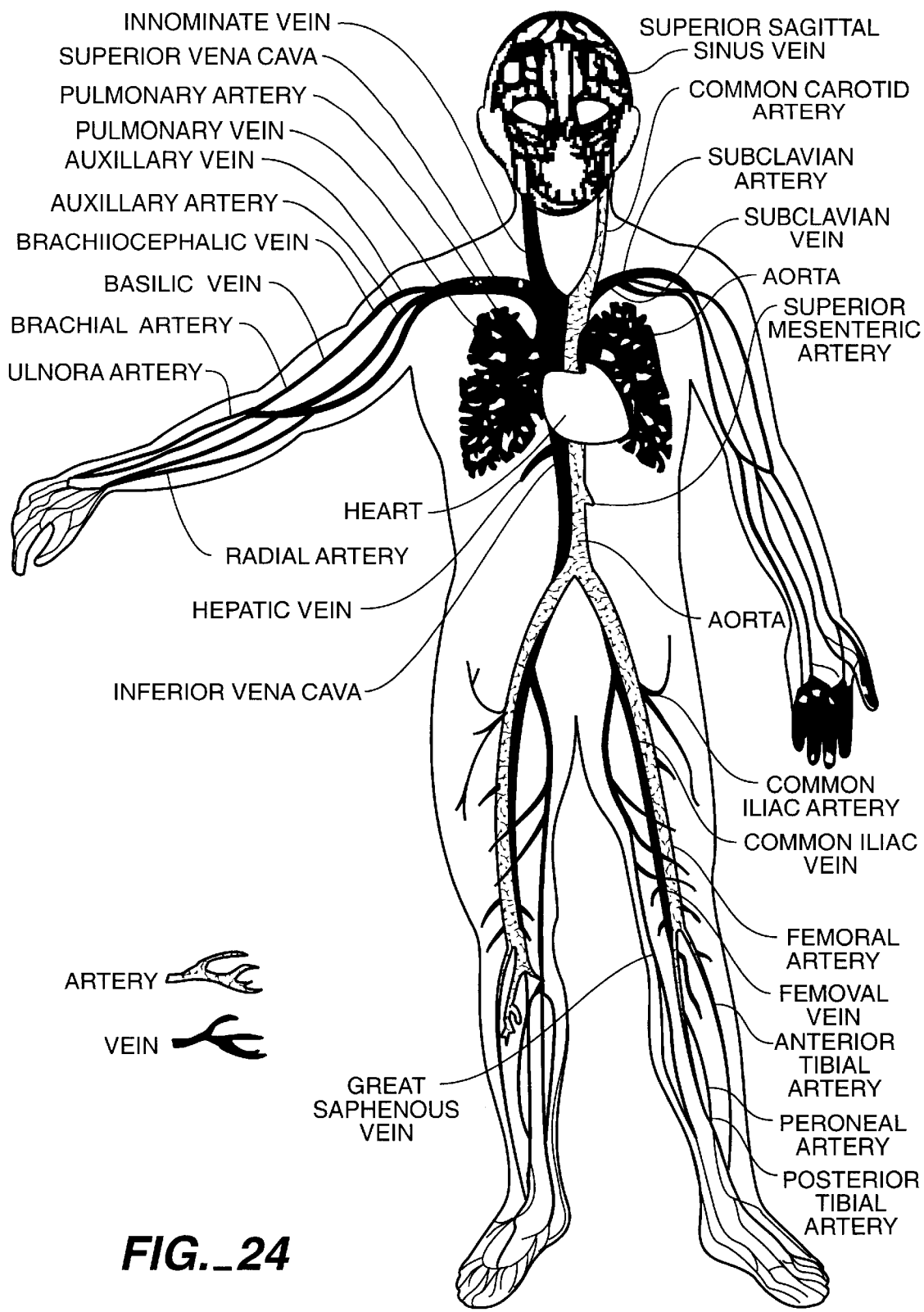
FIG._24

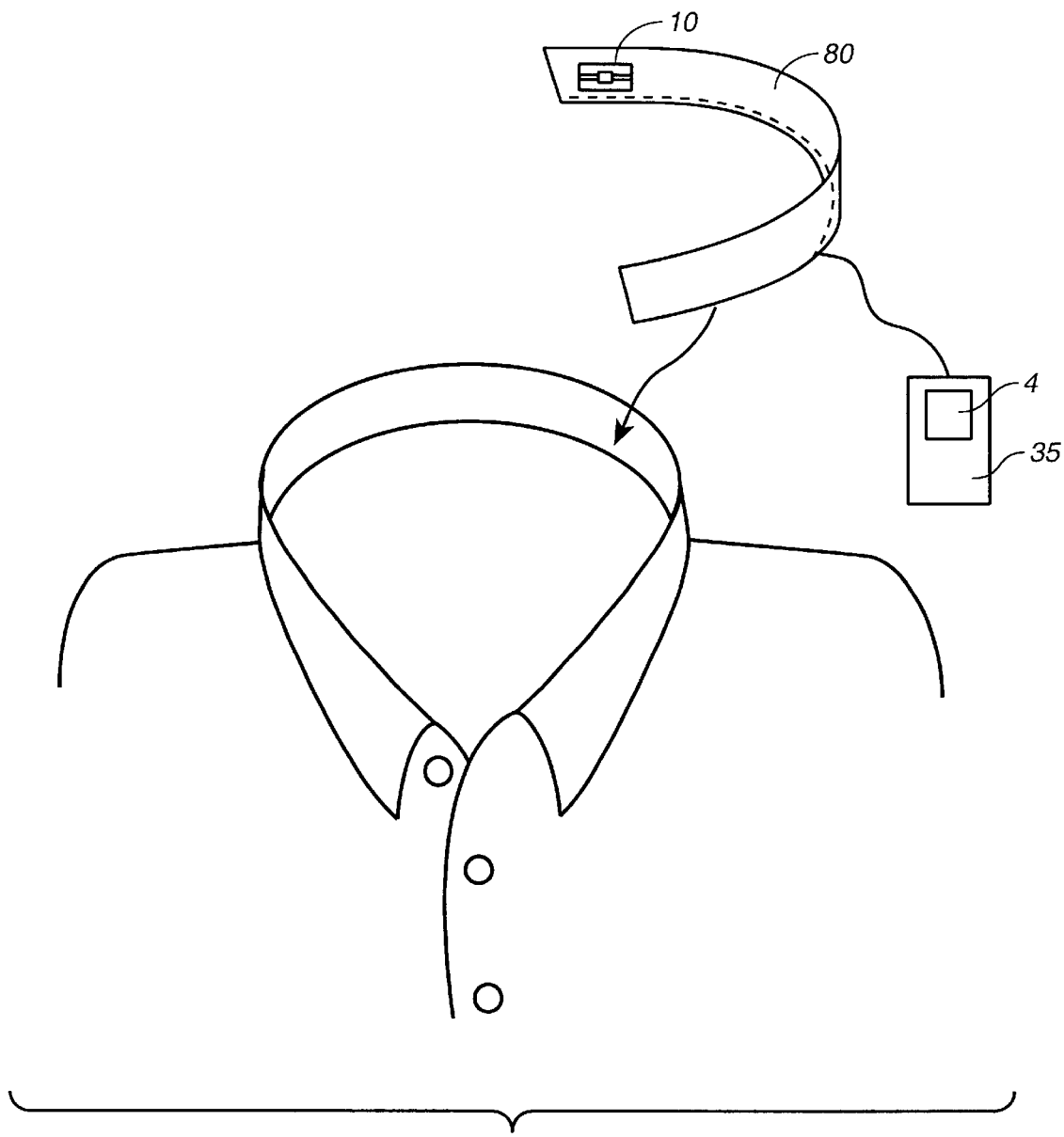
FIG._25
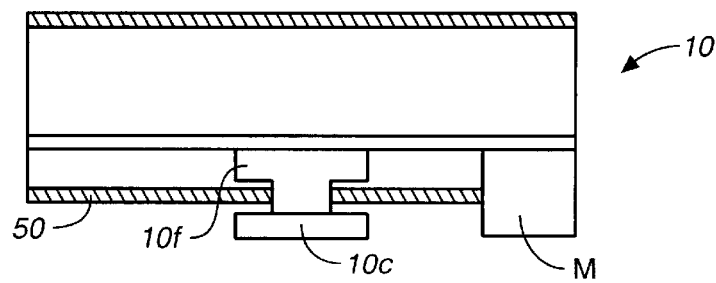
FIG._26

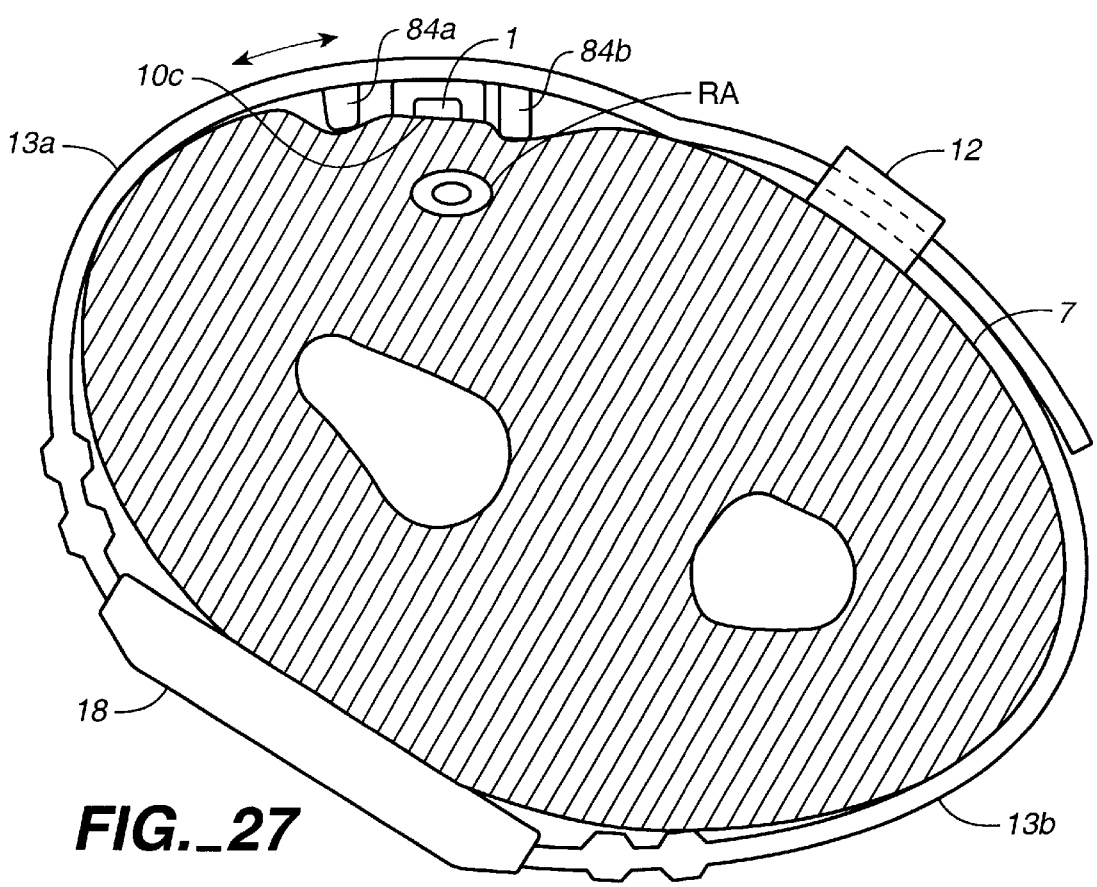
FIG._27

METHOD OF DETECTING PULSE WAVE, METHOD OF DETECTING ARTERY POSITION, AND PULSE WAVE DETECTING APPARATUS

TECHNICAL FIELD

The present invention relates to a method of detecting pulse wave, a method of detecting an artery position, and a pulse wave detecting apparatus, which enable a stable detection of the pulse wave irrespective of the operational level of an operator and are suitable for detecting a pulse waveform according to blood flow through an artery or blood vessels around the artery.

BACKGROUND ART

As one of the pulse wave detecting apparatuses, a device which detects the pulse wave of a radial artery is known. This device detects changes in pressure to the skin near the radial artery using a pressure sensor, thereby measuring the pulse wave. Since the device detects the change in the pressure applied to the sensor which is placed on the skin above the radial artery, a pressing force of 30 mmHg to 80 mmHg is required in order to stably detect the pulse wave. This causes a strong constrictive feeling in the subject.

For example, in U.S. Pat. No. 4,951,679, a pressure sensor placed near the radial artery is pressed against the arm while varying the pressing force in sequence to detect the pressing force with the maximum amplitude of a detected signal. The pulse wave is detected with this pressing force. This allows an optimum pressing force to be set without applying unnecessary pressure. However, it is necessary to apply a predetermined pressure against the arm, thereby leaving the problem of a strong constrictive feeling.

On the contrary, some pulse wave detecting apparatuses utilizing ultrasound or light (such as infrared radiation and laser beams) do not require a strong pressing force. In a pulse wave detecting apparatus which uses a reflected wave of ultrasound, a probe that emits ultrasound is applied to the arm of a subject from the outer side and the probe receives the ultrasound reflected by an artery or the like to measure the pulse wave.

On the other hand, a pulse wave detecting apparatus which uses light emits a light from a light emitting diode, for example, to the inside of a body to detect the amount of reflected light (reflected light from subcutaneous tissues). Since part of the light emitted from the light emitting diode is absorbed by hemoglobin in the blood vessels, the amount of reflected light is related to blood capacity in the blood vessels to be detected as the pulse wave.

In a conventional pulse wave detecting apparatus using ultrasound, the detected values of the reflected wave vary in accordance with angles between a probe which transmits and receives ultrasound and blood flow. In the operation of the probe, it is difficult to maintain a fixed angle to the blood flow, thereby causing difficulty in stable measurement of the pulse wave. For example, in the case where the probe is applied to the palm side of a subject's arm, the detection of the pulse wave becomes difficult if the probe shifts only by several millimeters from an artery. In the case where the probe is applied to the backhand side of the subject's arm, a signal-to-noise (SN) ratio necessary for detecting the pulse wave can not be secured.

In a device utilizing a laser or light-emitting diode, if irradiating light is not applied to the artery, the SN ratio necessary for detecting the pulse waveform can not be secured or stable pulse waveform can not be detected.

Conventionally, the pulse waveform has been detected based on the blood flowing in the artery. According to traditional Oriental medicine, it is believed that the conditions of a living body can be monitored based on the pulse waveform. The artery formed of smooth muscles and the like supplies blood to the peripheral tissues by the pulsation. Since the artery is a tissue of the living body, it is necessary to provide the artery with blood. The arteriole supplies blood to the arterial tissues. Since the arteriole supplies blood to the artery itself, the condition of the artery can be monitored by detecting the pulse waveform based on the blood flow of the arteriole. However, in conventional methods for detecting pulse waves, the pulse waveform has been detected based on the blood flowing in the artery, but the pulse waveform based on blood flowing in the arteriole has not been detected.

The present invention has been achieved to solve the above-described problems. An object of the present invention is to provide a method of detecting a pulse wave, a method of detecting an artery position, and a pulse wave detecting apparatus, which enable stable detection of the pulse wave independent of the skill level of an operator without forcing a strong constrictive feeling on the subject, and are suitable for detecting the pulse waveform according to blood flow through an artery or blood vessels around the artery.

DISCLOSURE OF THE INVENTION (1) A method of detecting a pulse wave according to the present invention, uses a pulse wave detection means which detects a pulse waveform of blood flowing through blood vessels around an artery, and the method comprises steps of:

detecting the pulse waveform by the pulse wave detection means at a plurality of positions;

sensing a polarity of the pulse waveform detected by the pulse wave detection means; and detecting the pulse waveform detected in a position range from a position where the polarity is inverted to a position where the polarity is returned to an original polarity as the pulse waveform from the blood vessels around the artery.

According to the present invention, the polarity of the pulse waveform in the blood vessels around an artery is sensed, the pulse waveform being detected at a plurality of positions and the pulse waveform in the blood vessels around the artery are detected in a position range from a position where the polarity is inverted to a position where the polarity is returned to the original polarity, that is, in the position range in which the polarity inversion resulting from the compression due to the artery is observed. This allows the pulse waveform from blood flowing through the arteriole, which is the blood vessel surrounding the artery, to be reliably detected with a high signal-to-noise ratio.

(2) A method of detecting a pulse wave according to the present invention, comprises steps of:

detecting a pulse waveform by a pulse wave detection means which detects the pulse waveform from blood flowing through blood vessels around an artery at a plurality of detection positions;

sensing a polarity of the pulse waveform detected by the pulse wave detection means; and detecting the pulse wave of the artery positioned approximately at a center of the blood vessels around the artery in a position range from a position where the polarity is inverted to a position where the polarity is returned to an original polarity.

According to the present invention, the polarity of the pulse waveform in the blood vessels around an artery is sensed, the pulse waveform being detected at a plurality of positions and the pulse waveform in the artery positioned approximately at the center of the blood vessels around the artery are detected in a position range from a position where the polarity is inverted to a position where the polarity is returned to the original polarity, that is, in the position range in which the polarity inversion resulting from the compression due to the artery is observed. This allows the pulse wave of the artery to be detected at the accurately specified position, so that the pulse waveform of the artery can be reliably detected with a high signal-to-noise ratio.

(3) A method of detecting a position of an artery according to the present invention, using a pulse wave detection means which detects a pulse waveform of blood flowing through blood vessels around the artery, comprises the steps of:

detecting the pulse waveform by the pulse wave detection means at a plurality of positions;

sensing a polarity of the pulse waveform detected by the pulse wave detection means; and detecting the location of the artery in a position range from a position where the polarity is inverted or is in the process of being inverted to a position where the polarity is returned to an original polarity.

According to the present invention, the polarity of the pulse waveform of the blood vessels around an artery is sensed, the pulse waveform being detected at a plurality of positions and the location of the artery is detected in a position range from a position where the polarity is inverted or is in the process of being inverted to a position where the polarity is returned to the original polarity, that is, in the position range in which the polarity inversion or its process of inversion resulting from the compression due to the artery is observed. This allows the position of the artery positioned approximately at the center of arterioles adjacent to and surrounding the artery to be reliably detected.

(4) A pulse wave detecting apparatus according to the present invention comprises:

a pulse wave detection means for detecting a pulse waveform of blood vessels around an artery from a detection part of a living body at a plurality of positions; and a pulse wave waveform display means for displaying the pulse waveform.

According to the present invention, the pulse waveform of the blood vessels around an artery at a plurality of positions which has been detected by the pulse wave detection means can be monitored through the pulse waveform display means. Therefore, the pulse waveform from the arterioles adjoining the periphery of the artery can be easily detected by recognizing the polarity inversion of the pulse waveform.

(5) A pulse wave detecting apparatus according to the present invention comprises:

a pulse wave detection means for detecting a pulse waveform of blood vessels around an artery from a detection part of a living body at a plurality of positions;

a polarity detection means for detecting a polarity of the pulse waveform which is output from the pulse wave detection means; and an announcement means for announcing a detection result of the polarity detection means.

According to the present invention, the polarity, detected by the polarity detection means can be monitored through the announcement means, for the pulse waveform of the blood vessels around the artery at a plurality of positions detected by the pulse wave detection means. Therefore, the polarity inversion of the pulse waveform can be easily recognized so that the pulse waveform from the arterioles adjoining around the artery can be reliably detected.

(6) In the pulse wave detecting apparatus described above, it is preferable to further comprise a position change means for changing a relative position between the pulse wave detection means and the detection part.

According to the present invention, the pulse waveform of the blood vessels around the artery can easily be detected at a plurality of positions by changing the relative position between the pulse wave detection means and the detection part by the position change means.

(7) In the pulse wave detecting apparatus described above, it is preferable that the position change means changes the relative position between the pulse wave detection means and the detection part so as to exist within a position range from a position where the polarity detected by the polarity detection means is inverted to a position where the polarity is returned to the original polarity.

According to the present invention, the position change means changes the relative position between the pulse wave detection means and the detection part so as to locate within a position range from a position where the polarity is inverted to a position where the polarity is returned to the original polarity, that is, within the position range where the polarity inversion resulting from the compression due to the artery is observed. Therefore, the pulse wave detection means allows the pulse waveform from blood flowing through the arterioles, which are the blood vessels surrounding the artery, to be reliably detected with a high signal-to-noise ratio.

(8) In the pulse wave detecting apparatus described above, it is preferable that the apparatus further comprise a body movement elimination means for eliminating a component due to body movement from the pulse waveform detected by the pulse wave detection means to create a body movement eliminated pulse waveform, and the polarity detection means detects a polarity based on the body movement eliminated pulse waveform.

According to the present invention, the polarity detection means detects the polarity based on the body movement eliminated pulse waveform in which the component due to the body movement have been eliminated by the body movement elimination means. Therefore, the polarity detection means can detect the polarity reliably even if there are body movements.

(9) The pulse wave detecting apparatus according to the present invention comprises:

a pulse wave detection means for detecting a pulse waveform of blood vessels around an artery from a detection part of a living body at a plurality of positions;

a polarity detection means for detecting a polarity of the pulse waveform which is output from the pulse wave detection means;

an amplitude detection means for detecting an amplitude of the pulse waveform which is output from the pulse wave detection means; and an announcement means for announcing a detected result of the polarity detection means and a detected result of the amplitude detection means.

According to the present invention, the polarity detected by the polarity detection means and the amplitude of the pulse waveform detected by the amplitude detection means for the pulse waveform of the blood vessels around the artery at a plurality of positions detected by the pulse wave detection means can be monitored through the announcement means. Therefore, the polarity inversion and the amplitude change of the pulse waveform can easily be recognized so that the pulse waveform from the arteriole adjoining around the artery can be reliably detected with a high signal-to-noise ratio.

(10) The pulse wave detecting apparatus according to the present invention comprises:

- a pulse wave detection means for detecting a pulse waveform of blood vessels around an artery from a detection part of a living body at a plurality of positions;
- a polarity detection means for detecting a polarity of the pulse waveform which is output from the pulse wave detection means; and
- a position change means for changing the relative position between of the pulse wave detection means and the detection part approximately to a center position in a position range from a position where the polarity detected by the polarity detection means is inverted to a position where the polarity is returned to the original polarity.

According to the present invention, the position change means changes the relative position between the pulse wave detection means and the detection part to the center position in the position range from a position where the polarity is inverted to a position where the polarity is returned to the original polarity, that is, to the center position in the position range where the polarity inversion resulted from the compression due to the artery is observed based on the polarity detected by the polarity detection means for the pulse waveform of the blood vessels around the artery at a plurality of positions detected by the pulse wave detection means. Therefore, the pulse wave detection means can reliably detect with a high signal-to-noise ratio the pulse waveform from blood flowing through arterioles surrounding the circumference of the artery.

(11) The pulse wave detecting apparatus according to the present invention comprises:

- a pulse wave detection means for detecting a pulse waveform of blood vessels around an artery from a detection part of a living body at a plurality of positions;
- a polarity detection means for detecting a polarity of the pulse waveform which is output from the pulse wave detection means;
- an amplitude detection means for detecting an amplitude of the pulse waveform which is output from the pulse wave detection means; and
- a position change means for changing the relative position between the pulse wave detection means and the detection part so that the relative position resides in a position range from a position where the polarity detected by the polarity detection means is inverted to a position where the polarity is returned to an original polarity and the amplitude detected by the amplitude detection means is made substantially maximized.

According to the present invention, the position change means changes the relative position between the pulse wave detection means and the detection part so that the relative position resides in the position range from a position where the polarity is inverted to a position where the polarity is returned to the original polarity, that is, in the position range where the polarity inversion resulting from the compression due to the artery is observed and the amplitude detected by the amplitude detection means is made a maximum based on the polarity detected by the polarity detection means for the pulse waveform of the blood vessels around the artery at a plurality of positions detected by the pulse wave detection means. Therefore, the pulse wave detection means can reliably detect with a high signal-to-noise ratio the pulse waveform from the blood flow flowing through arterioles surrounding the periphery of the artery.

(12) In the pulse wave detecting apparatus described above, it is preferable to comprise a body movement elimination means for eliminating a component due to a body movement from the pulse waveform detected by the pulse wave detection means to create a body movement eliminated pulse wave waveform, wherein the polarity detection means detects a polarity based on the body movement eliminated pulse wave waveform, and wherein the amplitude detection means detects an amplitude based on the body movement eliminated pulse wave waveform.

According to the present invention, the polarity detection means detects the polarity and the amplitude detection means detects the amplitude based on the body movement eliminated pulse waveform in which the component due to the body movement is eliminated from the pulse waveform by the body movement elimination means. Therefore, even if there are body movements, the polarity detection means can properly detect the polarity and the amplitude detection means can accurately detect the amplitude.

(13) In the pulse wave detecting apparatus described above, it is preferable that the body movement elimination means comprises a body movement detection section for detecting the body movement of the living body, a first frequency analysis section for performing a frequency analysis of a body movement waveform detected by the body movement detection section, a second frequency analysis section for performing a frequency analysis of a pulse waveform detected by the pulse wave detection means, and a body movement elimination section creating the body movement eliminated pulse waveform by comparing frequency analysis results analyzed by the first frequency analysis section and the second frequency analysis section.

According to the present invention, frequency analysis of the body movement waveform detected by the body movement detection section is performed by the first frequency analysis section, and frequency analysis of the pulse waveform detected by the pulse wave detection means is performed by the second frequency analysis section, so that the body movement elimination section can accurately create the body movement eliminated pulse wave waveform by comparison of those analysis results.

(14) In the pulse wave detecting apparatus described above, it is preferable that the first and second frequency analysis sections perform frequency analysis using FFT.

(15) In the pulse wave detecting apparatus described above, it is preferable that the position change means move while stopping for a discontinuance time which is at least a minimum period of time to perform the FFT.

According to the present invention, the FFT can be properly performed at each position changed by the position change means.

(16) In the pulse wave detecting apparatus described above, it is preferable that the first and second frequency analysis sections perform frequency analysis using wavelet transformation.

(17) In the pulse wave detecting apparatus described above, it is preferable that the position change means moves while stopping for a discontinuance time which is at least a minimum period of time to perform the wavelet transformation.

According to the present invention, the wavelet transformation can be properly performed at each position changed by the position change means.

(18) In the pulse wave detecting apparatus described above, it is preferable that the body movement elimination means comprises:
- a frequency analysis section for performing frequency analysis of the pulse waveform from the pulse wave detection means; and
- a body movement separation section creating the body movement eliminated pulse waveform based on a frequency component from which a low frequency component is eliminated in a frequency analysis result analyzed by the frequency analysis section.

According to the present invention, the body movement separation section eliminates a low frequency component from the frequency analysis result analyzed by the frequency analysis section, so that the body movement elimination means can create the body movement eliminated pulse waveform from which a component due to the body movement, having a high probability of existing in a lower frequency range than a basic frequency component of the pulse waveform, are substantially eliminated. Therefore, the present invention can create the body movement eliminated pulse waveform with a simple configuration without using the body movement detection section and the first frequency analysis section required by the body movement elimination means described above.

(19) In the pulse wave detecting apparatus described above, it is preferable that the body movement separation section determine the maximum frequency of the low frequency component based on a basic frequency of the pulse waveform detected by the pulse wave detection means.

According to the present invention, in the body movement separation section, it is noticed that when the pulse is increased by exercise or the like, the consequent frequency of the basic component of the pulse waveform rises and the frequency component of the body movement is also increased, since the body is active during exercise. Therefore, the maximum frequency of the low component to be eliminated is determined based on the basic frequencies of the pulse waveform detected by the pulse wave detection means. This allows body movement component to be eliminated with a high probability even if the frequencies of component due to the body movements by exercise or the like are increased.

(20) In the pulse wave detecting apparatus described above, it is preferable that the frequency analysis section perform frequency analysis using FFT or wavelet transformation.

(21) In the pulse wave detecting apparatus' described above, it is preferable that the pulse wave detection means be an optical type pulse wave detection means detecting a pulse wave of blood vessels around an artery based on a light absorption property of blood flowing through the blood vessels around the artery.

According to the present invention, a pressing force is not required to be applied to the detection part as with a pulse wave detection means of the compression sensor type since a pulse wave detection means of the optical type is used. Thus, pulse wave can be detected without causing a constrictive feeling to a subject, and the pulse wave detection means can be easily moved in order to detect the pulse wave at a plurality of positions.

(22) In the pulse wave detecting apparatus described above, it is preferable that the pulse wave detection means be set so that a detection wavelength exists in a wavelength range from 300 nm to 700 nm.

According to the present invention, the detected wavelength of the optical type pulse wave detection means is set in the wavelength range from 300 nm to 700 nm, the absorption ratio of the wavelength range is high due to the hemoglobin in the blood, so that the absorbed amount of light detected by the pulse wave detection means greatly varies according to the amount of blood in the blood vessels. Accordingly, the pulse waveform can be detected accurately.

In addition, as the light with a wavelength below 700 nm is difficult to transmit through the tissue of a living body, pulse wave from blood vessels around an artery, which blood vessels exist in an area shallower than the artery, can be detected and are free from the influence of the outside light.

(23) In the pulse wave detecting apparatus described above, it is preferable to further comprise an artery pulse wave detection means for detecting a pulse wave of an artery positioned approximately at a center of blood vessels around the artery, and
   wherein the artery pulse wave detection means is provided substantially at the same position as the pulse wave detection means and the relative position between the artery pulse wave detection means and the detection part is changed by the position change means.

According to the present invention, the artery pulse wave detection means for detecting pulse wave of an artery positioned approximately at the center of the blood vessels around the artery is provided substantially at the same position as the pulse wave detection means, and the relative position between the artery pulse wave detection means and the detection part is changed by the position change means. Accordingly, when the pulse wave detection means is moved by the position change means to a position at which the pulse waveform of arterioles positioned around the artery is to be measured, the artery pulse wave detection means can accurately detect the pulse wave of the artery positioned approximately at the center of the arterioles.

BRIEF DESCRIPTION OF THE DRAWINGS

FIG. 1 is a perspective view of a model of a radial artery;

FIG. 2 is a cross-sectional illustration schematically showing positions of a radial artery, arterioles and capillary vessels;

FIG. 3 is a schematic illustration showing the pulsation of the radial artery;

FIG. 4 is an illustration showing pulse waveform of a capillary vessel, arteriole and boundary region;

FIG. 5 is a block diagram showing an electrical configuration of the pulse wave detecting apparatus according to a first embodiment;

FIG. 6 is a circuit diagram of the pulse wave detector according to the first embodiment;

FIG. 7 is a circuit diagram of a polarity detection section according to the first embodiment;

FIG. 8 is a perspective view showing the appearance of the pulse wave detecting apparatus according to the first embodiment;

FIG. 9 is a perspective view showing a condition in which the pulse wave detecting apparatus according to the first embodiment is mounted on an arm;

FIG. 10 shows the relationship between the pulse waveform and a polarity detection signal in the first embodiment;

FIG. 11 is a block diagram showing an electrical configuration of the pulse wave detecting apparatus according to a second embodiment;

FIG. 12 is a front view showing the appearance of the automatic position change mechanism according to the second embodiment;

FIG. 13 is a schematic view showing a modification of the pulse wave detection section;

FIG. 14 is a block diagram showing the electrical configuration of the pulse wave detecting apparatus according to a third embodiment;

FIG. 15 is a schematic view showing a pulse wave detection section and an artery pulse wave detection section according to the third embodiment;

FIG. 16 is a block diagram showing the electrical configuration of the pulse wave detecting apparatus according to a forth embodiment;

FIG. 17 is a block diagram showing Construction Example 1 of the body movement elimination section according to the fourth embodiment;

FIG. 18 is a block diagram showing a detailed configuration of a first frequency analysis section according to the fourth embodiment;

FIG. 19 is a timing chart for explaining the operation the body movement elimination section according to the fourth embodiment;

FIG. 20 shows pulse wave analysis data MKD at period Tc in the fourth embodiment;

FIG. 21 shows body movement analysis data TKD at period Tc in the fourth embodiment;

FIG. 22 shows body movement eliminated pulse wave analysis data MKDj in the fourth embodiment;

FIG. 23 is a block diagram showing Construction Example 2 of the body movement elimination section according to the fourth embodiment;

FIG. 24 is an illustration showing arteries of a human body;

FIG. 25 shows the appearance configuration of a pulse wave detecting apparatus according to a modification;

FIG. 26 shows the mechanical configuration of an automatic position change mechanism 10 according to the modification;

FIG. 27 is a cross-sectional view in a condition in which a pulse wave detecting apparatus of a photoelectric reflection type is mounted on an arm.

BEST MODE FOR CARRYING OUT THE INVENTION

A. Principle

First, the method of detecting pulse wave of arterioles according to the present invention will be explained. In the present embodiment, the pulse wave of arterioles surrounding a radial artery will be detected. FIG. 1 is a perspective view of a model of a radial artery 24. Blood flows in an endothelium 100. The endothelium 100 is covered by a tunica intima 101, and an internal elastic membrane 102 is formed outside thereof. A tunica media 103 is formed between the internal elastic membrane 102 and an external elastic membrane 104. The tunica media 103 is composed of smooth muscles arranged thickly in line. A tunica adventitia 105 is formed outside of the external elastic membrane 104, and arterioles AR are formed inside the tunica adventitia 105. When the radial artery 24 contracts, the internal elastic membrane 102 and the external elastic membrane 104 strongly wave, and when it is expanded, they are extended tabularly. The radial artery 24 supplies blood to tissues by such pulsation, but it is necessary to supply blood to the radial artery 24 itself. It is the arteriole AR that bears this role.

FIG. 2 is a cross-sectional illustration schematically showing positions of the radial artery 24, arterioles AR and capillary vessels CA, CAp. An inner wall RA of the radial artery 24 is composed of the endothelium 100 and the tunica intima 101. As shown in this figure, the arterioles AR are formed outside the inner wall RA of the radial artery 24, and a plurality of capillary vessels CA, CAp are formed inside a skin S. In this example, the capillary vessels CAp existing between the inner wall RA of the radial artery 24 and the skin S, and the capillary vessels CA existing at a position apart from the inner wall RA of the radial artery 24 are shown distinctively.

The capillary vessels CA, CAp are mesh-shaped and supply the blood carried by the radial artery 24 to each tissue. Therefore, pulse waveform detected from the radial artery 24 and from the capillary vessels CA have the same polarities, although there is little delay time.

Blood flow initiated by contraction and expansion of the heart flows in the radial artery 24, so that a pulsation shown in FIG. 3 proceeds toward the peripheries at a velocity range of 8 to 16 m/s. In this figure, when the inner wall RA of the radial artery 24 is expanded by the pulsation as shown by a position X1, the arterioles AR and the capillary vessels CAp positioned in the neighborhood of the position X1 are put in an ischemic state by pressure on the inner wall RA of the radial artery 24. On the other hand, as shown by a position X2, when the inner wall RA of the radial artery 24 is not expanded, the arterioles AR and the capillary vessels CAp are not pressed by the inner wall RA of the radial artery 24, causing an ordinary blood flow.

For this reason, the polarity of the pulse waveform of the radial artery 24 is inverted when compared with that of the pulse waveform of the arterioles AR and the capillary vessels CAp. On the other hand, as described above, the polarity of the pulse waveform of the radial artery 24 corresponds to that of the capillary vessels CA. Accordingly, as with the pulse waveform shown in FIG. 4, the polarity of the pulse waveform of the capillary vessels CA is inverted compared to that of the pulse waveform of the arterioles AR.

When the pulse waveform inside a very shallow part is measured from the surface of the skin S around the arm, as shown in FIG. 2, there are areas W1, W3 in which the pulse waveform of the capillary vessels CA are measured and an area W2 in which the pulse waveform of the arterioles AR and the capillary vessels CAp are measured. In this case, when the pulse waveform are measured from a position Xs toward a position Xe (in the circumferencial direction), the polarity of the pulse waveform are inverted at the area W2. Therefore, the position of the radial artery 24 can be specified by detecting the position at which the polarity of the pulse waveform is inverted.

In the actual detection of the pulse waveform, in the vicinity of the boundary region of the region in which the pulse waveform of the capillary vessels CA are detected and the region in which the pulse waveform of the arterioles AR and the capillary vessels CAp are detected, that is, in the vicinity of the boundary region of the W1 and W2 and the boundary region of the W2 and W3, pulse waveform are synthesized which are substantially equal in phase (pulse waveform of the arterioles AR and the capillary vessels CAp are more or less delayed with respect to those of the capillary vessels CA) and are opposite in polarity to form a waveform in which they cancel each other. Accordingly, as shown in FIG. 4, in these boundary regions, the pulse waveform in the process of being inverted is observed as a feeble signal with very small amplitude. When considering this condition, in detecting the pulse waveform inside a very shallow part from the surface of the skin S around the arm, it can be specified that there is an artery surrounded by blood vessels in the region from which the waveform of this boundary region or the waveform with an inverted polarity can be obtained.

In addition, the pulse waveform detected in such a position range is detected according to the blood flows of the arterioles AR and the capillary vessels CAp. Here, the arteriaoles AR serve to supply blood to the radial artery 24, as described above, so that the condition of the radial artery 24 can be accurately apprehended by analyzing the pulse waveform. For example, the analysis serves to diagnose arteriosclerosis and to reveal the degree of tension of the artery due to a psychological effect.

From the medical point of view described above, the inventors of the present invention noted the results of considering capillary vessels CA, CAP, the inner wall RA of the radial artery 24 and the arterioles AR and developed a method of detecting pulse wave which easily detects the pulse waveform of the arterioles. The feature of this method of detecting pulse wave is such that, when the pulse waveform is detected from a detection part of a living body using a moveable pulse wave detection section a light with a specific wavelength is used as a detection light and the relative position between the pulse wave detection section and the detection part is changed in order to invert the polarity of the detected pulse waveform.

B. First Embodiment

The pulse wave detecting apparatus according to a first embodiment of the present invention will be described with reference to the drawings.

B1. Configuration of the Pulse Wave Detecting Apparatus

B1-1 Electrical Configuration

FIG. 5 is a block diagram showing the electrical configuration of the pulse wave detecting apparatus according to the first embodiment. A pulse wave detection section 1 as a pulse wave detection means shown in this figure detects pulse waveform MH of the capillary vessels CA, CAp and the arterioles AR. The pulse wave detection section 1 comprises an LED 32 (light emitting section), a phototransistor 33 (light receiving section) and the like, as shown in FIG. 6. In this figure, when a switch SW is turned ON to apply the power voltage, light is emitted from the LED 32 and, after being reflected by blood and tissues, it is received by the phototransistor 33, causing the pulse waveform MH to be detected. Here, the wavelength of emission of the LED is selected to be approximately the absorption peak by wavelength of hemoglobin in the blood. Therefore, the light receiving level is changed according to the amount of blood flow. Accordingly, the pulse waveform can be detected by detecting the light receiving level.

In addition, as the LED 32, a blue LED of an InGaN system (indium-gallium-nitrogen system) is preferable. The emission spectrum of the blue LED has an emission peak at, for example, 450 nm and its emission wavelength range is from 350 nm to 600 nm. One of the phototransistor 33 corresponding to the LED with such an emission characteristic is a phototransistor of a GaAsP system (gallium-arsenic-phosphorus system). The light receiving wavelength range of this phototransistor 33 has, for example, a main sensibility range from 300 nm to 600 nm and is also sensible to a wavelength range below 300 nm. When such a blue LED and the phototransistor 33 are combined, the pulse wave is detected in the overlapped range of the wavelength range from 300 nm to 600 nm. In this case, there are the following advantages.

First, as discussed hereinbefore with respect to FIG. 2, the arterioles AR are formed as if they surround the blood vessel wall of the radial artery 24 from outside, and the capillary vessels CAp are formed between the inner wall RA of the radial artery 24 and the skin S. As such, when the light irradiated for detecting the pulse waveform MH of the arterioles AR and the capillary vessels CAp reaches the inner wall RA of the radial artery 24, it ends up detecting the blood flow. Since the polarities of the pulse waveform of the radial artery 24 and the capillary vessels CA are identical as described above, when the irradiated light reaches the inside of the radial artery 24, the polarity of the pulse waveform MH is not inverted at the position of the radial artery 24, even if the pulse wave detection section 1 is moved in the direction of the circumference of the arm, so that the position of the radial artery 24 can not be specified. However, the light with a wavelength below 700 nm is in general difficult to transmit through tissues of a living body, so that it can reach only a depth of about 2 mm to 3 mm from the surface of the skin. In addition, the radial artery 24 usually exists in a position deeper than 3 mm from the surface of the skin. Therefore, when the range of the detected light (overlapping area of the irradiated light and light receiving sensibility) is set in a wavelength range from 300 nm to 600 nm, the pulse waveform MH of the capillary vessels CA, CAp and the arterioles AR can be detected without being affected by the blood flow of the radial artery 24.

Similarly, the light with a wavelength below 700 nm included in the outside light tends to be difficult to transmit through the tissue of a living body, so that even if the outside light irradiates a part of the skin not covered by a shade part (a band described below), it does not reach the phototransistor 33 through the tissue of the living body, and only light which does not influence the detection reaches the phototransistor 33. On the other hand, most of the light with a wavelength range less than 300 nm is absorbed on the surface of the skin, so that even if the light receiving wavelength range is below 700 nm, the substantial light receiving wavelength range is in the range of 300 nm to 700 nm. Therefore, the influence of the outside light can be suppressed without covering the detection part completely.

In addition, the hemoglobin in the blood has a large absorption coefficient to light with a wavelength range from 300 nm to 700 nm, and the absorption coefficient is more than several times to approximately 100 times larger than that of light with a wavelength of 880 nm. Thus, as with the present embodiment, when the light with the wavelength range (300 nm to 700 nm) having a large absorption property is used as a detection light according to the absorption property of the hemoglobin, the detected values are sensitively varied according to changes in the amount of blood, so that the SN ratio of the pulse waveform MH based on the changes in amount of blood can be enhanced.

Next, a manual position change mechanism 2 as a position change means is a mechanism that can manually change the relative position of the pulse wave detection section 1 to the radial artery 24. The manual position change mechanism 2 in the present embodiment has a mechanical configuration which will be described hereinafter.

Then, a polarity detection section 3 as a polarity detection means detects the polarity of the pulse waveform MH to output a polarity detection signal KS. FIG. 7 is a circuit diagram of the polarity detection section 3. As shown in this figure, the polarity detection section 3 comprises an operational amplifier 30 to which power voltages of +V and −V are supplied, and resistors R1, R2. Positive feedback is provided by connecting the output of the operational amplifier 30 to the positive input through the resistors R1, R2, thereby constituting a hysteresis comparator. The hysteresis comparator has two thresholds L1, L2 (L1>L2), and its output signal is made high-level when an input signal goes over L1, and is made low-level when the input signal goes below L2. In the present embodiment, when resistance values of the resistors R1, R2 are assumed to be R1, R2, the thresholds L1, L2 are given from the following equations.

$$L1 = +V \cdot R2/(R1+R2)$$

$$L2 = -V \cdot R2/(R1+R2)$$

Therefore, when the pulse waveform MH goes over the threshold L1, the polarity detection signal KS becomes high-level, and when it goes below the threshold L2, the polarity detection signal KS becomes low-level.

A display 4 as an announcement means comprises a liquid crystal display device. In this display 4, there are displayed the polarity detected by the polarity detection section 2 and the living body information such as the amplitude values and pulse rate of the pulse waveform MH of the radial artery 24. The polarities are displayed by signs, for example, such as "+" and "−". Thus, when a subject operates the manual position change mechanism 2, the polarity of the pulse waveform MH detected by the pulse wave detection section 1 is displayed on the display 4, the subject can determine the position at which the polarity is inverted, that is the position of the radial artery 24. Further, a reference numeral 8 is a living body information generating section and generates information about a living body such as the amplitude values and pulse rate according to the pulse waveform MH.

According to the above described configuration, when a subject operates the manual position change mechanism 2, the polarity of the pulse waveform MH detected by the pulse waves detection section 1 is detected by the polarity detection section 3 to be displayed on the display 4. The waveform of the pulse wave of the arterioles AR around the inner wall RA of the radial artery 24 and the capillary vessels CAp has an inverted polarity as compared to that of the capillary vessels CA, so that the subject can view the position in which the polarity is inverted displayed on the display 4 as the position of the radial artery 24. Accordingly, the pulse wave detection section 1 can be positioned above the radial artery 24. In addition, when the positioning is required to be more precise, the positioning can be performed so that the amplitude values of the pulse waveform MH displayed on the display 4 are made maximum.

B1-2 Mechanical Configuration

FIG. 8 is a perspective view showing the appearance of the pulse wave detecting apparatus according to the present embodiment. As shown in this figure, the pulse wave detecting apparatus of the present embodiment has the configuration of a wristwatch. A main body 18 shown in this figure accommodates the polarity detection section 3 and display 4 described above. A clock IC, not shown, is provided in the main body 18, and the display 4 displays time information output by the clock IC, as shown in FIG. 8. An operation button 11 is provided for various operations such as switching between a measure mode for measuring pulse wave and a clock mode for displaying time.

Further, a pair of bands 13a, 13b are attached to the main body 18, and, as shown in FIG. 9, these are mounted on an arm by binding them to the arm and securing them with a clasp 12. A reference numeral 14 is a cylinder-shaped slide body with a rectangular cross-section, the slide body being movable along the band 13a, 13b, and the pulse wave detection section 1 is provided in this slide body 14. Therefore, when the slide body 14 is moved, the pulse wave detection section 1 also moves. This pulse wave detection section 1 comprises an optical sensor, so that there is no projection such as a pressure sensor. Thus, the slide body 14 can be moved smoothly without generating a constricting feeling to a subject, during the positioning. Additionally, a cable not shown is provided between the pulse wave detection section 1 and the main body 18, causing the detected pulse waveform MH to be transmitted.

B2. Operation of the Pulse Wave Detecting Apparatus

The operation of the pulse wave detecting apparatus of the first embodiment will be described. First, the bands 13a, 13b are bound to an arm and secured with the clasp 12. Then, the positioning mode is chosen by operating the operation button 11. As a result, a light from the light emitting section (LED 32) in the pulse wave detection section 1 irradiates the arm of the subject, and its reflected light is received in the light receiving section (phototransistor 33). As blood flowing through blood vessels has an absorption property which absorbs light as described above, the reflected light reaching the light receiving section is attenuated due to absorption by the blood flowing through the capillary vessels CA, CAp and the arterioles AR. The amount of attenuation becomes a function of the blood capacity of the part in the blood vessel through which the irradiated light penetrates, that is, corresponds to pulse wave of the blood flowing through the capillary vessels CA, CAp and the arterioles AR.

Here, it is assumed that the slide body 14 is positioned at a position Xs shown in FIG. 2 and is moved to a position Xe. In this case, the pulse waveform MH detected by the pulse wave detection section 1 will depend on the shift speed of the slide body 14. If the slide body 14 is moved at a sufficiently low speed, the pulse waveform MH detected by the pulse wave detection section 1 will be the pulse waveform MH which is marked "MH" in FIG. 10. L1 and L2 shown in FIG. 10 are threshold values of the hysteresis comparator used in the polarity detection section 3.

The output of the hysteresis comparator becomes high-level when the amplitude of the pulse waveform MH goes over the threshold value L1 and becomes low-level when it goes below the threshold value L2, so that the polarity detection signal KS shows the waveform with mark KS in FIG. 10. In this figure, periods T1, T3 in which the polarity detection signal KS is high-level correspond to the areas W1, W3 shown in FIG. 2, on the other hand, a low-level period T2 corresponds to the area W2.

In this case, "+" is displayed on the display 4 in periods T1 and T2 and "−" is displayed in period T2. However, the thickness of a radial artery 24 is small with respect to the distance moved by the slide body 14, so that the period T2 will be very short. Therefore, the subject can find the position of the radial artery 24 by moving the slide body 14 while observing the polarity displayed on the display 4.

After the slide body 14 is moved above the radial artery 24 in this manner, the pulse wave detection mode is chosen by operating the operation button 11. Then, the amplitude value of the pulse waveform MH detected by the pulse wave detection section 1 is shown on the display 4. Thus, the subject can detect a more precise pulse waveform MH of the arterioles AR by fine-tuning the position of the slide body 14 so as to maximize the amplitude of the pulse waveform MH.

B3. Modifications of the First Embodiment (1) One example of the announcement means As explained previously, according to the present embodiment, the positional relationship of the pulse wave detection section 1 and the arterioles AR (the positional relationship of the pulse wave detection section 1 and the radial artery 24) is displayed to the operator. However, as an alternative, the present embodiment may be configured to alert the operator by sound. That is, a pronouncing section which the pronounces according to the polarity detection signal KS of the polarity detection section 3 may be provided. In addition, the pronouncing section is configured to present the positional relationship of the pulse wave detection section 1 and the arterioles AR, for example, by changing sound attributes such as volume, pitch, and tone according to the level of the polarity detection signal KS. It may also be configured to alert the subject by changing the sound interval, for example, of an electronic bleep.

(2) One example of the positioning method of the pulse wave detection section 1

As explained previously, according to the present embodiment, the position of the pulse wave detection section 1 can be advantageously set while observing the display 4, however, it is preferable that the irradiated light be made to penetrate in the vicinity of the radial artery 24 as closely as possible in the initial positioning when the device is mounted on the arm. In this case, for the present standard, marks may be placed on the band 13a. That is, as shown in FIG. 9, scales 13m, 13m, . . . are placed on the band 13a at predetermined intervals, and the position on the scale at which the slide body 14 has been initially positioned is remembered. Then, immediately after the bands 13a, 13b are mounted on the arm, the position of the slide body 14 is adjusted to the position on the scale. Only a small amount of adjustment of the slide body 14 is there fore required after switched to the measure mode, resulting in rapid measurement.

C. Second Embodiment

C1. Configuration of the Pulse Wave Detecting Apparatus

FIG. 11 is a block diagram showing the electrical configuration of the pulse wave detecting apparatus according to a second embodiment. The present embodiment is provided with an automatic position change mechanism 10 and a controller 6, in place of the slide body 14 (manual position change mechanism 2) in the configuration of the first embodiment described above.

The automatic position change mechanism 10 as a position change means drives the pulse wave detection section 1 in the circumferencial direction of the arm (in the direction perpendicular to the radial artery 24), and is driven by the controller 6. The controller 6 generates a pulse drive signal DS according to the polarity signal KS so as to position the pulse wave detection section 1 at the center of an interval in which the polarity of the polarity signal KS is inverted.

Here, FIG. 12 is a front view (skin side) showing the appearance of the automatic position change mechanism 10, through which the band 13b penetrates as shown in the figure. A linear pulse motor is incorporated in the automatic position change mechanism 10, and 10b shown in the figure is its slider. This linear pulse motor changes the excitation condition of the inside coil by the pulse drive signal DS, precisely advances by a constant pitch. A movable section 10c is provided in the skin side of the slider 10b, and the pulse wave detection section 1 is attached to this movable section 10c. The movable section 10c can be moved along a groove 10a in the horizontal direction in the figure with a stroke of approximately 1 cm.

C2. Operation of the Pulse Wave Detecting Apparatus

In the above described configuration, when the positioning mode is set, the controller 6 outputs the drive signal DS to initialize the automatic position change mechanism 10. Specifically, the movable section 10c shown in FIG. 12 is shifted to the right end of the groove 10a.

Then, the controller 6 controls the automatic position change mechanism 10 so as to cause the movable section 10c to move from right to left at a constant speed. In this case, the travelling speed of the movable section 10c is set so that inversion of the pulse waveform MH can be detected. When the movable section 10c starts travelling, the polarity detection section 3 detects its polarity according to the pulse waveform MH from the pulse wave detection section 1 to generate the polarity signal KS.

When the polarity signal KS is supplied to the controller 6, it causes the movable section 10c to travel to the left until the polarity signal KS is inverted. The diameter of the blood vessel of the inner wall RA of the radial artery 24 is smaller than the stroke (1 cm) of the movable section 10c, and the mounting position of the automatic position change mechanism with respect to the band 13b is set so that the center of the automatic position change mechanism 10 is almost in line with the radial artery 24. For this reason, it is very rare that the pulse wave detection section 1 is located above the radial artery 24 when the movable section 10c is initialized, so the movable section 10c is located at position Xs shown in FIG. 2 when it is initialized. Accordingly, when the movable section 10c starts to travel from the initial position, first, the pulse waveform MH of the capillary vessels CA is detected by the pulse wave detection section 1. When the movable section 10c travels further, the pulse waveform MH of the arterioles AR and the capillary vessels CAp are detected. At this time, the polarities of the pulse waveform MH of the capillary vessels CA and the pulse waveform MH of the arterioles AR and the capillary vessels CAp are opposite to each other, so that when the polarity signal KS is inverted, the movable section 10c is positioned above the left end of the radial artery 24.

When the controller 6 detects the inversion of the polarity signal KS, it starts to count the number of pulses of the pulse drive signal DS and continues the count operation until the polarity of the polarity signal KS is re-inverted. The polarity of the polarity signal KS is re-inverted when the pulse waveform MH detected by the pulse wave detection section 1 is switched from the arterioles AR and the capillary vessels CAp to the capillary vessels CA. That is, at this timing, the movable section 10c is positioned above the right end of the radial artery 24.

Thereafter, the controller 6 sets the counted pulse rate of the pulse drive signal DS to one-half and generates the pulse drive signal DS so as to cause the movable section 10c to travel in the reverse direction by this pulse rate. This enable the movable section 10c to travel just above the radial artery 24, resulting in the precise detection of the pulse waveform MH of the arterioles AR.

As a result of the operation described above, the pulse wave detection section 1 is controlled to the position in which the pulse waveform MH is maximized. In the present embodiment, as different from a device in which positioning is performed using a pressure sensor (e.g., U.S. Pat. No. 4,951,679), when positioning is performed, the pulse wave detection section 1 is not pressed against the skin, so that only a small amount of power is required to move the movable section 10c along the skin. Therefore, sufficient servo control is available with the torque of a usual linear pulse motor. In addition, the optimum position of the pulse wave detection section 1 can be determined when the moving distance, i.e., stroke, of the movable section 10c is approximately 1 cm with respect to the diameter of an artery.

C3. Modifications of the Second Embodiment (1) In the second embodiment, display of the amplitude values on the display 4 may be omitted. This is because the pulse wave detection section 1 is automatically driven to the optimum position by the servo mechanism so that it is not necessary for a user to monitor the amplitude values. However, if the amplitude values are displayed on the display 4, the operating condition of the servo mechanism can be ascertained, and if the servo mechanism is defective, the position of the pulse wave detection section 1 can be optimized manually.

(2) In the second embodiment, the amplitude values of the pulse waveform MH detected in the pulse wave detection section 1 may be supplied to the controller 6 (refer to the dotted line in FIG. 11) to generate the pulse drive signal DS according to this amplitude values and the polarity signal KS. In this case, when the controller 6 detects the inversion of the polarity signal KS, the pulse waveform MH of the arterioles AR formed inside of the tissue of the blood vessel of the radial artery 24 will be detected. Then, the controller 6 causes the movable section 10c to shift by one pitch to the right and judges whether or not the amplitude value of the pulse waveform MH becomes larger. If this value becomes larger, the movable section 10c is further shifted by one more pitch to the right and a measurement is made as to whether or not the amplitude value becomes larger. In similar fashion, the movable section 10c is shifted to the right, and when the amplitude value becomes small, the movable section 10c is returned to the left by one pitch, and the shift operation is completed. As a result of the operation described above, the pulse wave detection section 1 is controlled to the position at which the amplitude value of the pulse waveform MH becomes maximum.

During exercising such as running, a belt bound on an arm may sometimes slip due to the swinging of the arm. Under such circumstances, the position of the pulse wave detection section 1 may slip from just above the radial artery 24, causing the SN ratio of the pulse waveform MH to deteriorate. In this case, the controller 6 may detect that the amplitude value of the pulse waveform is lowered below a predetermined value from the previous mean amplitude value. This leads to perform the position change of the pulse wave detection section 1, again based on the amplitude value described above.

(3) In the embodiment described above, the pulse waveform in a plurality of positions have been detected by the pulse wave detection section 1 by moving the pulse wave detection section 1 with respect to the detection part using the automatic position change mechanism 10. However, as a modification corresponding to FIG. 12, as shown in FIG. 13, a pulse wave detection section 46 is formed by forming a plurality of pairs of light emitting elements and light receiving elements into an array-shaped configuration. The pulse waveform in a plurality of positions can be detected by controlling which pair of the light emitting element and light receiving element are available. In this case, the automatic position change mechanism 10 is not required, and the controller 6 may be provided with a function for controlling which pair of a plurality of the light emitting elements and light receiving elements provided in the pulse wave detection section 46 are selected.

D. Third Embodiment

D1. Configuration of the Pulse Wave Detecting Apparatus

FIG. 14 is a block diagram showing the electrical configuration of the pulse wave detecting apparatus 60 according to a third embodiment. The present embodiment is different from the pulse wave detecting apparatus 40 of the second embodiment in that an artery pulse wave detection section 62 is provided in addition to the pulse wave detection section 1, a living body information generating section 8 generates living body information by receiving information from an artery pulse wave detection section 62, and the display 4 displays the body information. Other arrangements are the same as those of the second embodiment, so further explanation is omitted. Parts corresponding to the second embodiment are denoted by the same reference numerals.

The pulse wave detection section 1 and the artery pulse wave detection section 60 of the present embodiment are provided at the position of the pulse wave detection section 1 shown in FIG. 12 in the second embodiment, and placed at substantially the same position adjacent to each other as shown in FIG. 15. Each of these pulse wave detection section 1 and artery pulse wave detection section 60 are attached to the movable section 10c as in the second embodiment. Therefore, the relative positions of the pulse wave detection section 1 and the artery pulse wave detection section 62 with respect to the part to be detected are changed by the automatic position change mechanism 10 in the same manner as the pulse wave detection section 1 is shifted in the second embodiment.

The artery pulse wave detection section 62 detects the pulse waveform MHa of an artery, for example a radial artery 24, positioned substantially at the center of arterioles AR (refer to FIG. 2). The artery pulse wave detection section 62 comprises, for example, a LED or EL (light emitting section) and a phototransistor (light receiving section). In the artery pulse wave detection section 62, the detection wavelength range, which is the range in which the light emitting wavelength range of the light emitting section and the detection wavelength range of the light receiving section overlap, is selected so that the light absorption due to hemoglobin in an artery at a depth from the skin corresponding to, for example, a position of the radial artery 24 can be detected. Thus, the light receiving level is changed according to the amount of blood flow of an artery, for example, the radial artery 24. For this reason, the pulse waveform of an artery, for example, the radial artery, can be detected by detecting the light receiving level.

D2. Operation of the Pulse Wave Detecting Apparatus

When the pulse wave detecting apparatus 60 having the configuration described above is set in the positioning mode, the controller 6 outputs the drive signal DS for initializing the automatic position change mechanism 10. Specifically, the movable section 10c shown in FIG. 12 is shifted to the right end of the groove 10a.

Then, the controller 6 controls the automatic position change mechanism 10 so as to cause the movable section 10c to move from right to left at a constant speed. In this case, the travelling speed of the movable section 10c is set so that inversion of the pulse waveform MH which is detected by the pulse wave detection section, can be detected. When the movable section 10c starts travelling, the polarity detection section 3 detects its polarity according to the pulse waveform MH from the pulse wave detection section 1 to generate the polarity signal KS.

When the polarity signal KS is supplied to the controller 6, it causes the movable section 10c to move leftwards until the polarity signal KS is inverted. The diameter of the blood vessel of the inner wall RA of the radial artery 24 is smaller than the stroke (1 cm) of the movable section 10c, and the installed position of the automatic position change mechanism 10 with respect to the band 13b is set so that the center of the automatic position change mechanism 10 is made to substantially agree with the radial artery 24. For this reason, it is very rare for the pulse wave detection section 1 or the artery pulse wave detection section 62 to be located above the radial artery 24 when the movable section 10c is initialized and located at the right end of the groove 10a. Thus, the movable section 10c is located at a position Xs shown in FIG. 2 when it is initialized. When the movable section 10c starts to travel from the initial position, first, the pulse waveform MH of the capillary vessels CA is detected by the pulse wave detection section 1. Then, when the movable section 10c travels further, the pulse waveform MH of the arterioles AR and the capillary vessels CAp are detected by the pulse wave detection section 1 and the pulse wave of the radial artery 24 are detected by the artery pulse wave detection section 60. As mentioned before, the polarities of the pulse waveform MH of the capillary vessels CA and the pulse waveform MH of the arterioles AR and the capillary vessels CAp are opposite to each other, so that when the polarity signal KS is inverted, the movable section 10c is positioned above the right end of the radial artery 24.

When the controller 6 detects the inversion of the polarity signal KS, it starts to count the number of pulses of the pulse drive signal DS and continues to count until the polarity of the polarity signal KS is re-inverted. The polarity of the polarity signal KS is re-inverted when the pulse waveform MH detected by the pulse wave detection section 1 is switched from the arterioles AR and the capillary vessels CAp to the capillary vessels CA. That is, at this timing, the movable section 10c is positioned above the left end of the radial artery 24.

Thereafter, the controller 6 sets the counted pulse rate of the pulse drive signal DS to one-half and generates the pulse drive signal DS so as to cause the movable section 10c to travel in the reverse direction by this pulse rate. This enables the movable section 10c to travel just above the radial artery 24. At this position, the artery pulse wave detection section 62 can accurately detect the pulse waveform MHa from the radial artery 24 with a high SN ratio.

E. Fourth Embodiment

Each embodiment described above detects the polarity of the pulse waveform MH detected by the pulse wave detection section 1 and positions the pulse wave detection section 1 according to the detected result. Since the blood flowing in the capillary vessels CA, CAp and arterioles AR is affected by body movement when the doby moves, body movement components overlap the pulse waveform MH, causing the amplitudes of the pulse waveform MH to strongly fluctuate independent of the pulsation. In such a case, when the polarity is determined according to the output of the pulse wave detection section 1, the polarity may not be judged correctly because of the influence of the body movement. Then, in a fourth embodiment, even if there are body movements, positioning of the pulse wave detection section 1 is precisely performed by detecting the polarity after the body movement components are eliminated.

An electrical configuration of a pulse wave detecting apparatus 65 according to the fourth embodiment is shown in FIG. 16. The configuration of this pulse wave detecting apparatus 65 is same as the pulse wave detecting apparatus of the second embodiment described above except that a body movement elimination section 7 is provided between the pulse wave detection section 1 and the polarity detection section 3. The body movement elimination section 7 eliminates the waveform of body movements from the pulse waveforms MH to generate body movement eliminated pulse wave waveform MHj. The following are configuration examples of specific configurations the body movement elimination section 7.

E1. Configuration Example 1 of the Body Movement Elimination Section 7

FIG. 17 is a block diagram showing a Construction Example 1 of the body movement elimination section 7. A body movement detection section 70 shown in this figure is provided inside the main body 18 (refer to FIG. 8) and is comprises an acceleration sensor and the like. A body movement waveform TH showing body movements of a living body is detected by the body movement detection section 70.

In addition, a first frequency analysis section 71 performs the frequency analysis to the body movement waveform TH to generate body movement analysis data TKD. On the other hand, a second frequency analysis section 72 performs the frequency analysis to the pulse waveform MH to generate pulse wave analysis data MKD. For a method of frequency analysis, FFT (fast Fourier transformation) and wavelet transformation are available. In the present embodiment, the wavelet transformation will be explained as one example.

Generally, in a time frequency analysis which processes a signal from both time and frequency, a wavelet becomes a unit which cuts out a part of the signal. The wavelet transformation represents the magnitude of each part of the signal cut out by this unit. As a base function for defining the wavelet transformation, a function $\psi(x)$ which is localized in time and frequency is introduced as a mother wavelet. Here, the wavelet transformation due to the mother wavelet $\psi(x)$ of a function f(x) is defined as follows:

$$(W_\psi f)(b, a) = \int_{-\infty}^{\infty} \frac{1}{\sqrt{a}} \psi\left(\frac{x-b}{a}\right) f(x) dx \tag{1}$$

In Equation (1), "b" is a parameter used when the mother wavelet $\psi(x)$ is translated (parallel translation). On the other hand, "a" is a parameter when scale (expansion and retraction) is performed. Therefore, the wavelet $\psi((x-b)/a)$ in Equation 1 is made by parallel translating the mother wavelet $\psi(x)$ by "b" and scaling it by "a". In this case, the width of the mother wavelet $\psi(x)$ is extended corresponding to the scale parameter "a", so that 1/a corresponds to frequency.

In this paragraph, a detailed configuration of the first frequency analysis section 71 will be described. FIG. 18 is a block diagram showing the detailed configuration of the first frequency analysis section 71. The second frequency analysis section 72 is also configured similar to the first frequency analysis section 71. This first frequency analysis section 71 has the configuration for performing the operation process of Equation (1) described above, so that clock CK is supplied and the operation process is performed within the clock period. As shown in the figure, the first frequency analysis section 71 comprises a base function storage section W1 storing the mother wavelet $\psi(x)$, a scale conversion section W2 performing a conversion with a scale parameter "a", a buffer memory W3, a parallel translation section W4 performing a translation operation, and a multiplication section W5. As the mother wavelet $\psi(x)$ stored in the base function storage section W1, a Mexican hat, a Haar wavelet, a Meyer wavelet, and a Shannon wavelet, including a Gabor wavelet, are available.

First, when the mother wavelet $\psi(x)$ is read out from the base function storage section W1, then the scale conversion section W2 performs a conversion using the scale parameter "a". Here, since the scale parameter "a" corresponds to the period, the mother wavelet $\psi(x)$ is extended on the time axis when "a" becomes larger. In this case, since the amount of data of the mother wavelet ψ (x) stored in the base function storage section W1 is constant, when "a" becomes larger, the amount of data per unit time is reduced. The scale conversion section W2 performs an interpolation process to compensate for this reduction, and when "a" becomes smaller, it performs a thin out process to generate a function ψ (x/a). This data is temporarily stored in the buffer memory W3.

Next, the translation section W4 reads out the function ψ (x/a) from the buffer memory W3 at the timing corresponding to the translate parameter "b", and performs translation of the function ψ (x/a) to generate a function ψ((x−b/a).

Next, body movement waveform data THD, which is obtained by converting the body movement waveform TH through an A/D converter (not shown), is supplied to the multiplication section W5. The multiplication section W4 multiplies a variable $1/a^{1/2}$, a function ψ ((x−b/a) and the body movement waveform data THD to perform the wavelet transformation and to generate body movement analysis data TKD. In this example, the body movement waveform data TKD is divided into frequency ranges, such as 0 Hz to 0.5 Hz, 0.5 Hz to 1.0 Hz, 1.0 Hz to 1.5 Hz, 1.5 Hz to 2.0 Hz, 2.0 Hz to 2.5 Hz, 2.5 Hz to 3.0 Hz, 3.0 Hz to 3.5 Hz, and 3.5 Hz to 4.5 Hz, and is output. The second frequency analysis section 72 is also constituted similar to the first frequency analysis section 71.

Next, a body movement elimination section 73 shown in FIG. 17 subtracts the body movement analysis data TKD from the pulse wave analysis data MKD to generate body movement eliminated pulse wave analysis data MKDj, which is subjected to inverse wavelet transformation and D/A conversion to generate the body movement eliminated pulse waveform MHj. The inverse wavelet transformation has a complementary relationship with the wavelet transformation described above, and the following operation of Equation (2) is performed in the inverse wavelet transformation.

$$f(x) = \frac{1}{C_\psi} \int \int_{R^2} (W_\psi f)(b, a) \frac{1}{\sqrt{a}} \psi\left(\frac{x-b}{a}\right) da \frac{db}{a^2} \quad (2)$$

The operation of the Construction Example 1 the body movement elimination means will be explained with reference to the figures. In this example, it is assumed that a user elevates a cup by hand and then returns it to the original position. In this case, it is also assumed that the pulse waveform MH shown in FIG. 19 is detected by the pulse wave detection section 1, and at the same time, the body movement waveform TH shown in FIG. 19 is detected by the body movement detection section 70.

In FIG. 19, the body movement waveform TH begins to increase from time T1, reaches a positive peak at time T2, then gradually decreases to pass through level 0 at time T2, reaches a negative peak at time T3, and returns to level 0 at time T4. Since the body movement waveform TH is detected by an acceleration sensor or the like, time T3 corresponds to the time when the user elevates the cup to the maximum, time T1 corresponds to the time when the user starts to elevate the cup, and time T4 corresponds to the time when the user stops elevating the cup. Therefore, body movement resides in the period from time T1 to time T4. The pulse waveform MHj is the waveform to be obtained assuming body movement does not exist. Also, in this example, the basic frequency of the pulse waveform MH is 1.3 Hz.

Next, with reference to FIGS. 20 to 22, the operation of the pulse wave detecting apparatus in period Tc shown in FIG. 19 will be described. FIG. 20 shows the pulse wave analysis data MKD in period Tc, and FIG. 21 shows the body movement analysis data TKD in period Tc. From these figures, it will be understood that frequency components of a relatively large level exist in the frequency range of 0.0 Hz to 1.0 Hz in the body movement waveform TH.

When the pulse wave analysis data MKD and the body movement analysis data TKD are supplied to the body movement elimination section 73, the body movement elimination section 73 subtracts the body movement analysis data TKD from the pulse wave analysis data MKD to generate the body movement eliminated pulse wave analysis data MKDj. Even if there are body movements, this cancels the influence of the body movement and enables the body movement eliminated pulse wave analysis data MKDj to be obtained. Thereafter, the body movement elimination section 73 subjects the body movement eliminated pulse wave analysis data MKDj to inverse wavelet transformation to generate the body movement eliminated pulse waveform MHj shown in FIG. 21.

Thus, in the Construction Example 1, the body movement eliminated pulse waveform MHj is generated by eliminating the body movement components overlapping the pulse waveform MH according to the body movement waveform TH detected by the body movement detection section 70, so that even if there are body movements due to swinging of an arm, the position of the radial artery 24 can be detected precisely. This example is preferred when the automatic position change mechanism 10 is subjected to feedback control so as to maximize the amplitude values of the pulse waveform MH while detecting pulse wave.

E2. Construction Example 2 of the Body Movement Elimination Section

In the Construction Example 1, the body movement waveform TH is detected by the body movement detection section 70 and subjected to the wavelet transformation. Then, the results of the wavelet transformation of the pulse waveform MH and the body movement waveform TH are compared. The body movement components contained in the frequency components of the pulse waveform MH are cancelled to generate the body movement eliminated pulse waveform MHj. However, the Construction Example 1 requires the body movement detection section 70 and the first frequency analysis section 71, causing the configuration to be complicated. The Construction Example 2 has been made in an attempt to solve this problem. In the following explanation, the wavelet transformation will be explained as one example of frequency analysis, however, FFT may be used in place of the wavelet transformation, as with the Construction Example 1.

FIG. 23 is a block diagram showing the Construction Example 2 of the body movement elimination section 7. In this example, the body movement elimination section 7 comprises the second frequency analysis section 72 and a body movement separation section 74. The second frequency analysis section 72 is identical to the Construction Example 1. The body movement separation section 74 separates and eliminates the body movement components from the pulse wave analysis data MKD to generate the body movement eliminated pulse waveform MHj. The body movement separation section 74 utilizes a characteristic of body movement described below.

Body movements are generated by vertical movement of arms and swinging of arms during running. However, in daily life, a living body is not moved instantaneously. For this reason, in daily life, the frequency components of the body movement waveform TH are not very high, and are usually in a range of 0 Hz to 1 Hz. In addition, the basic frequency of the pulse waveform MH often exists in a range of 1 Hz to 2 Hz. Therefore, in daily life, the frequency components of the body movement TH reside in a lower frequency range than the basic frequency of the pulse waveform MH.

On the other hand, during sports such as jogging, the frequency components of the body movement waveform TH become somewhat higher due to influences such as swinging of the arms. However, since the heart rate increases according to the amount of movement, the basic frequency of the pulse waveform MH also increases at the same time. Thus, it is usual that, even during sport, the frequency components of the body movement waveform TH resides in a lower frequency range than the basic frequency of the pulse waveform MH.

The body movement separation section 74 separates the body movements in view of this point, and is configured to disregard the frequency range lower than the basic wavelength components of the pulse waveform MH. In this case, when the body movement components exist in a frequency range higher than the basic wavelength components of the pulse waveform MH, the detection accuracy of the pulse wave is lowered. However, as described above, since the body movement components have a high probability of existing in a lower frequency range than the basic wavelength components of the pulse waveform MH, the components due to body movement can be eliminated with high accuracy. That is, the body movement separation section 74 generates the body movement eliminated pulse waveform MHj according to the frequency components from which low frequency components are eliminated as a result of frequency analysis.

In FIG. 23, a waveform shaping section 741 subjects the pulse waveform MH to waveform-shaping to generate reset pulses synchronizing with the pulse waveform MH. A counter 742 counts clock pulses not shown and its count value is reset by the reset pulse. In addition, a mean value calculation circuit 743 calculates a mean value of count values of the counter 742. This mean value corresponds to a mean period of the pulse waveform MH. Therefore, the basic frequency of the pulse waveform MH can be detected in conjunction with the mean value.

Next, a substitution circuit 744 defines the frequency range including the basic wavelength frequency of the pulse waveform MH according to the mean value. For example, when the mean value shows 0.71 seconds, the basic wavelength frequency is 1.4 Hz, so that the frequency range defined becomes 1 Hz to 1.5 Hz. Then, the substitution circuit 744 generates body movement separation pulse wave data TBD by substituting the pulse wave analysis data MKD to "0" for a frequency range under the defined frequency range. This causes the components of the frequency range lower than the basic wavelength frequency of the pulse waveform MH to be disregarded. In this case, the pulse wave components as well as the body movement components are also substituted to "0" however, characteristic parts of the pulse waveform MH exist in a frequency range higher than the basic wavelength frequency, so that this scarcely affects the body movement eliminated pulse waveform MHj finally obtained even if they are substituted to "0". Subsequently, an inverse conversion section 745 subjects the body movement separation pulse wave data TBD to the inverse wavelet transformation to generate the body movement eliminated pulse waveform MHj.

In this manner, the Construction Example 2 generates the body movement eliminated pulse waveform MHj by the body movement separation section 74 without using the body movement detection section 70 and the first frequency analysis section 71, so that the position of the radial artery 24 can be detected precisely with a simple configuration. As with the Construction Example 1, this example is preferred when the automatic position change mechanism 10 is subjected to feedback control so as to maximize the amplitude values of the pulse waveform MH while detecting pulse wave.

E3. Modifications of the Fourth Embodiment (1) In the fourth embodiment described above, the pulse wave detecting apparatus including the automatic position change mechanism 10 as with the second embodiment has been explained as one example. However, the body movement elimination section 7 may be applied to the pulse wave detecting apparatus with the manual position change mechanism 2 explained in the first embodiment.

(2) In the fourth embodiment described above, the output of the wavelet transformation has a certain relationship between each frequency range and time range, so that detection time is defined according to a frequency range to be divided into. Accordingly, it is preferable to intermittently drive the automatic position change mechanism 10 for every detection time unit. In addition, when FFT is used as a technique of frequency analysis, it is preferable that the automatic position change mechanism 10 be intermittently driven for every detection time unit in which FFT can be performed.

F. Modifications

The present invention is not limited to the embodiments described above. The various modifications described below are possible.

(1) In each embodiment described above, a radial artery in the carpus as a part of a living body from which the pulse wave are detected has been explained as one example. However, the present invention is intended to detect the pulse waveform of the arterioles formed inside the blood vessel tissues of an artery, so that the part of a living body from which pulse wave are detected is not limited to this. That is, there are various types of human arteries as shown in FIG. 24. Thus, when formation of the pulse wave detecting apparatus described above is modified to fit the detection part, position of various arteries or arterioles surrounding the arteries can be defined, allowing precise detection of the pulse waveform.

For example, when a pulse waveform MH is detected from the carotid artery in the neck, a configuration shown in FIG. 25 is preferable. In this figure, an arch-shaped attachment part 80 is made to be attached to the inside part of a collar of clothing. The automatic position change mechanism 10 is attached to the inside of this attachment part 80. A code is drawn from the automatic position change mechanism 10 to be connected to a control box 35. The display 4 and the polarity detection section 3 are provided in the control box 35. The size of the control box 35 is set so that it can be put in a pocket. The operation of the present embodiment being the configuration described above is the same as that of the second embodiment.

Furthermore, in place of the automatic position change mechanism 10, the pulse wave detection section 1 may be moved manually as with the first embodiment. Additionally, as the attachment part 80 for detecting pulse wave from the carotid artery, not only the type described above but also shapes such as an annulus of a necklace, loop of a necktie, or collar may be used.

(2) Each embodiment described above employs an optical sensor as an example of the pulse wave detection section 1, however, as long as pulse wave of blood vessels positioned in a predetermined range of a depth from the skin can be detected, the present invention is not limited to this optical sensor, and, for example, a sensor using ultrasonic waves or pressure sensor may be used. Further, as an optical sensor, not only a sensor of a reflection type but also a transmission type may be used.

(3) Each embodiment described above senses the position of arterioles according to the polarity of the pulse waveform MH detected by the pulse wave detection section 1, however, a sensor for detecting the position of the arterioles may be further provided in addition to for the pulse wave detection section 1.

(4) The automatic position change mechanism 10 adopted in the second and fourth embodiments employs a configuration of a linear pulse motor, but alternatively, the movable section 10c may be driven by a mechanical configuration. One example of this case is shown in FIG. 26. In FIG. 26, a ball screw 50 is mounted on a shaft of a motor M with a common shaft center. The light receiving section 2 is attached to a base member 10f which engages with the ball screw 50. When the ball screw 50 rotates, the base member 10f is moved in the horizontal direction in the figure according to its rotational direction. The amount of movement is proportional to the amount of rotation of the ball screw 50. Further, the pulse wave detection section 1 is provided in the movable section 10c. The automatic position change mechanism 10, as configured in the above-described way, drives the movable section 10c in the circumferential direction of the arm (in the direction perpendicular to the radial artery 24).

In this case, as with the second embodiment, the movable section 10c is not pressed against the skin, so that only a small amount of power is required to move the movable section 10c along the skin. Therefore, sufficient servo control is available with the torque of a usual microminiature motor. In addition, the optimum position can be satisfactorily detected with a moving length of approximately 1 cm.

(5) In each embodiment and modification described above, pressure leg portions 84a, 84b shown in FIG. 27 may be provided at the ends of the slide body 14. FIG. 27 is a cross-sectional representation in a condition in which a photoelectric reflection type pulse wave detecting apparatus is mounted on an arm. In this figure, wrist bands 13a, 13b attached to both ends of the main body 18 are bound to the wrist of a subject and are secured with the clasp 12. The clasp 12 allows the peripheral length of the wrist bands 13a, 13b to be adjusted, that is, enables a constricting force to the wrist to be adjusted.

The optical type pulse wave detection section 1 is fixed to the reverse side (side facing the wrist) of the wrist band 13a. A transmission part and a receiving part are constituted integrally in the pulse wave detection section 1. The pulse wave detection section 1 presses the skin just above the radial artery 24 using the constricting force of the wrist band 13a, 13b.

The press leg portions 84a, 84b protruding to the reverse side are attached to the wrist band 13a. At least one of the pressure leg portions 84a, 84b is made movable in the circumferential direction of wrist band 13a and suspensible at the moved position.

In this case, since the pressure leg portions 84a, 84b extend over the high elastic (soft) surface of both sides of the radial artery 24 to make hollows, the pulse wave detection section 1 can be easily positioned just above the radial artery 24. In addition, since the end of the movable section 10c is positioned higher than the ends of the pressure leg portions 84a, 84b, the radial artery 24 with lower elasticity (hard) than other tissue can be simply positioned between the pressure leg portions 84a, 84b.

Thus, a broad positioning is performed by providing such pressure leg portions 84a, 84b at the ends of the slide body 14 (refer to FIG. 8). Subsequently by performing a precise positioning using the slide body 14, an accurate positioning can be easily executed, allowing the SN ratio of the pulse wave signals to be enhanced.

The radial artery 24 usually resides at a position approximately 3 mm below the skin, so that the positioning may be performed only by pressing the skin using the pressure leg portions 84a, 84b. In this case, although the SN ratio of the pulse wave signals more or less deteriorates when compared to the case in which both the slide body 14 and the pressure leg portions 84a, 84b are used, it causes few practical problems.

(6) In the first embodiment described above, the polarity of the pulse waveform MH from the pulse wave detection section 1 is detected by the polarity detection section 3 to be displayed on the display 4. However, the pulse waveform MH may be directly displayed on the display 4 as a pulse waveform display means. In this case, when the pulse wave detection section 1 is positioned above the radial artery 24, the polarity of the pulse waveform MH is inverted, so that a subject can position the pulse wave detection section 1. Also, in this case, the amplitude of the pulse waveform MH may be detected by the living body information generating section 8 to display this amplitude value on the display 4 with numerical values or bar graphs.

What is claimed is:

1. A method of detecting a pulse wave using a pulse wave detection means which detects a pulse waveform from blood flowing through blood vessels around an artery, said method comprising steps of:

detecting the pulse waveform by said pulse wave detection means at a plurality of positions;

sensing a polarity of the pulse waveform detected by said pulse wave detection means; and detecting said pulse waveform detected in a position range from a position where said polarity is inverted to a position where said polarity is returned to an original polarity as the pulse waveform from the blood vessels around the artery.

2. A method of detecting a pulse wave, comprising steps of:

detecting a pulse waveform by a pulse wave detection means which detects the pulse waveform from blood flowing through blood vessels around an artery at a plurality of detection positions;

sensing a polarity of the pulse waveform detected by said pulse wave detection means; and detecting the pulse wave of said artery positioned approximately at a center of the blood vessels around said artery in a position range from a position where said polarity is inverted to a position where said polarity is returned to an original polarity.

3. A method of detecting a position of an artery using a pulse wave detection means which detects a pulse waveform from blood flowing through blood vessels around said artery, said method comprising steps of:

detecting the pulse waveform by said pulse wave detection means at a plurality of positions;

sensing a polarity of the pulse waveform detected by said pulse wave detection means; and detecting the location of said artery in a position range from a position where said polarity is inverted or is in the process of being inverted to a position where said polarity is returned to an original polarity.

4. A pulse wave detecting apparatus, comprising:
a pulse wave detection means for detecting a pulse waveform of blood vessels around an artery from a detection part of a living body at a plurality of positions; and
a pulse wave waveform display means for displaying said pulse waveform.

5. A pulse wave detecting apparatus, comprising:
a pulse wave detection means for detecting a pulse waveform of blood vessels around an artery from a detection part of a living body at a plurality of positions;
a polarity detection means for detecting a polarity of the pulse waveform which is output from said pulse wave detection means; and
an announcement means for announcing a detection result of said polarity detection means.

6. The pulse wave detecting apparatus according to claim 5, further comprising a position change means for changing a relative position between said pulse wave detection means and said detection part.

7. The pulse wave detecting apparatus according to claim 6, wherein said position change means changes the relative position between said pulse wave detection means and said detection part so as to exist within a position range from a position where the polarity detected by said polarity detection means is inverted to a position where the polarity is returned to the original polarity.

8. The pulse wave detecting apparatus according to claim 5, further comprising a body movement elimination means for eliminating a component due to body movement from the pulse waveform detected by said pulse wave detection means to create a body movement eliminated pulse waveform,
wherein said polarity detection means detects a polarity based on said body movement eliminated pulse waveform.

9. A pulse wave detecting apparatus, comprising:
a pulse wave detection means for detecting a pulse waveform of blood vessels around an artery from a detection part of a living body at a plurality of positions;
a polarity detection means for detecting a polarity of the pulse waveform which is output from said pulse wave detection means;
an amplitude detection means for detecting an amplitude of the pulse waveform which is output from said pulse wave detection means; and
an announcement means for announcing a detected result of said polarity detection means and a detected result of said amplitude detection means.

10. A pulse wave detecting apparatus, comprising:
a pulse wave detection means for detecting a pulse waveform of blood vessels around an artery from a detection part of a living body at a plurality of positions;
a polarity detection means for detecting a polarity of the pulse waveform which is output from said pulse wave detection means; and
a position change means for changing the relative position between said pulse wave detection means and said detection part approximately to a center position in a position range from a position where the polarity detected by said polarity detection means is inverted to a position where the polarity is returned to the original polarity.

11. A pulse wave detecting apparatus, comprising:
a pulse wave detection means for detecting a pulse waveform of blood vessels around an artery from a detection part of a living body at a plurality of positions;
a polarity detection means for detecting a polarity of the pulse waveform which is output from said pulse wave detection means;
an amplitude detection means for detecting an amplitude of the pulse waveform which is output from said pulse wave detection means; and
a position change means for changing the relative position between said pulse wave detection means and said detection part so that the relative position resides in a position range from a position where the polarity detected by said polarity detection means is inverted to a position where the polarity is returned to an original polarity and the amplitude detected by said amplitude detection means is made substantially maximized.

12. The pulse wave detecting apparatus according to claim 9, comprising a body movement elimination means for eliminating a component due to a body movement from the pulse waveform detected by said pulse wave detection means to create a body movement eliminated pulse waveform,
wherein said polarity detection means detects a polarity based on said body movement eliminated pulse waveform, and
wherein said amplitude detection means detects an amplitude based on said body movement eliminated pulse waveform.

13. The pulse wave detecting apparatus according to claim 8, wherein said body movement elimination means comprises:
a body movement detection section for detecting said body movement of the living body;
a first frequency analysis section for performing a frequency analysis of a body movement waveform detected by said body movement detection section;
a second frequency analysis section for performing a frequency analysis of a pulse waveform detected by said pulse wave detection means; and
a body movement elimination section for creating said body movement eliminated pulse waveform by comparing frequency analysis results analyzed by said first frequency analysis section and said second frequency analysis section.

14. The pulse wave detecting apparatus according to claim 13, wherein said first frequency analysis section and said second frequency analysis section perform frequency analysis using FFT.

15. The pulse wave detecting apparatus according to claim 5, further comprising a body movement elimination means for eliminating a component due to body movement from the pulse waveform detected by said pulse wave detection means to create a body movement eliminated pulse waveform,
wherein said body movement elimination means comprises:
a body movement detection section for detecting said body movement of the living body;
a first frequency analysis section for performing a frequency analysis of a body movement waveform detected by said body movement detection section;

a second frequency analysis section for performing a frequency analysis of pulse waveform detected by said pulse wave detection means; and a body movement elimination section for creating said body movement eliminated pule waveform by comparing frequency analysis results analyzed by said first frequency analysis section and said second frequency analysis section, wherein said first frequency analysis section and said second frequency analysis section perform frequency analysis using FFT, and wherein said position change means moves while stopping for a discontinuance time which is at least a minimum period of time to perform the FFT.

16. The pulse wave detecting apparatus according to claim 13, wherein said first frequency analysis section and said second frequency analysis section perform frequency analysis using wavelet transformation.

17. The pulse wave detecting apparatus according to claim 5, further comprising a body movement elimination means for eliminating a component due to body movement from the pulse waveform detected by said pulse wave detection means to create a body movement eliminated pulse waveform, wherein said body movement elimination means comprises:

a body movement detection section for detecting said body movement of the living body;

a first frequency analysis section for performing a frequency analysis of a body movement waveform detected by said body movement detection section;

a second frequency analysis section for performing a frequency analysis of a pulse waveform detected by said pulse wave detection means; and a body movement elimination section for creating said body movement eliminated pulse waveform by comparing frequency analysis results analyzed by said first frequency analysis section and said second frequency analysis section, wherein said first frequency analysis section and said second frequency analysis section perform frequency analysis using wavelet transformation, and wherein said position change means moves while stopping for a discontinuance time which is at least a minimum period of time to perform the wavelet transformation.

18. The pulse wave detecting apparatus according to claim 8, wherein said body movement elimination means comprises:

a frequency analysis section for performing frequency analysis of the pulse waveform from said pulse wave detection means; and a body movement separation section creating said body movement eliminated pulse waveform based on a frequency component from which a low frequency component is eliminated in a frequency analysis result analyzed by said frequency analysis section.

19. The pulse wave detecting apparatus according to claim 18, wherein said body movement separation section determines the maximum frequency of said low frequency component based on a basic frequency of the pulse waveform detected by said pulse wave detection means.

20. The pulse wave detecting apparatus according to claim 18, wherein said frequency analysis section performs frequency analysis using FFT or wavelet transformation.

21. The pulse wave detecting apparatus according to claim 4, wherein said pulse wave detection means is an optical type pulse wave detection means for detecting a pulse wave of blood vessels around an artery based on a light absorption property of blood flowing through the blood vessels around the artery.

22. The pulse wave detecting apparatus according to claim 21, wherein said pulse wave detection means is set so that detection wavelength exists in a wavelength range from 300 nm to 700 nm.

23. The pulse wave detecting apparatus according to any one of claims 6 to 8, 10 and 11, further comprising an artery pulse wave detection means for detecting a pulse wave of an artery positioned approximately at a center of blood vessels around said artery, and wherein said artery pulse wave detection means is provided substantially at the same position as said pulse wave detection means and said relative position between said artery pulse wave detection means and said detection part is changed by said position change means.

* * * * *

UNITED STATES PATENT AND TRADEMARK OFFICE
CERTIFICATE OF CORRECTION

PATENT NO. : 6,334,850 B1
DATED : January 1, 2002
INVENTOR(S) : Kazuhiko Amano et al.

It is certified that error appears in the above-identified patent and that said Letters Patent is hereby corrected as shown below:

<u>Title page,</u>
Item [56], FOREIGN PATENT DOCUMENTS, please add:
-- JP 8-187230 7/1996 --
-- JP 8-289876 11/1996 --
-- JP 1-122704 8/1989 --

Signed and Sealed this

Twenty-eighth Day of January, 2003

JAMES E. ROGAN
*Director of the United States Patent and Trademark Office*